(12) United States Patent
Annapragada et al.

(10) Patent No.: US 7,138,136 B2
(45) Date of Patent: Nov. 21, 2006

(54) AGGLOMERATED PARTICLES FOR AEROSOL DRUG DELIVERY

(75) Inventors: Annanth Annapragada, Shaker Heights, OH (US); Rohan Bhavane, Parma Mts, OH (US)

(73) Assignee: Cleveland State University, Cleveland, OH (US)

( * ) Notice: Subject to any disclaimer, the term of this patent is extended or adjusted under 35 U.S.C. 154(b) by 304 days.

(21) Appl. No.: 10/382,088

(22) Filed: Mar. 5, 2003

(65) Prior Publication Data

US 2003/0190284 A1    Oct. 9, 2003

Related U.S. Application Data

(60) Provisional application No. 60/361,961, filed on Mar. 5, 2002.

(51) Int. Cl.
*A61K 9/27* (2006.01)
*A61B 8/00* (2006.01)
*A61L 9/04* (2006.01)

(52) U.S. Cl. .................. 424/450; 424/9.51; 424/45

(58) Field of Classification Search ............... 424/450, 424/489, 9.52, 9.51, 9.32, 9.321, 45
See application file for complete search history.

(56) References Cited

U.S. PATENT DOCUMENTS

| | | | |
|---|---|---|---|
| 4,895,719 A | 1/1990 | Radhakrishnan | |
| 5,006,343 A | 4/1991 | Benson et al. | |
| 5,043,165 A | 8/1991 | Radhakrishnan | |
| 5,049,389 A | 9/1991 | Radhakrishnan et al. | |
| 5,059,421 A | 10/1991 | Loughrey et al. | |
| 5,192,528 A | 3/1993 | Radhakrishnan et al. | |
| 5,340,587 A | 8/1994 | Mihalko et al. | |
| 5,654,007 A | 8/1997 | Johnson et al. | |
| 5,874,064 A | 2/1999 | Edwards et al. | |
| 5,902,605 A | 5/1999 | Dong et al. | |
| 5,985,309 A | 11/1999 | Edwards et al. | |
| 6,090,407 A | 7/2000 | Knight et al. | |
| 6,103,270 A | 8/2000 | Johnson et al. | |
| 6,120,751 A | 9/2000 | Unger | |
| 6,136,294 A | 10/2000 | Adjei et al. | |
| RE37,053 E | 2/2001 | Hanes et al. | |
| 6,211,296 B1 | 4/2001 | Frate et al. | |
| 6,254,854 B1 | 7/2001 | Edwards et al. | |
| 6,290,987 B1 | 9/2001 | Modi et al. | |
| 2003/0138490 A1* | 7/2003 | Hu et al. .................. 424/486 |

FOREIGN PATENT DOCUMENTS

WO    WO0023052    4/2000

OTHER PUBLICATIONS

International Search Report dated Sep. 17, 2003.
Annapragada, et al., "Engineered Particles for Pulmonary Drug Delivery," Apr. 2001, www.whitaker.org/abstracts/apr01/annaprag.html.
Annapragada, et al., Abstract: "Respiratory Drug Deliver" www.aiche.org/conferences/techprogram/paperdetail.asp?PaperID=3396&DSN=annual01.
Parmar, et al., "Incorporated of bacterial membrane proteins into liposomes: factors influencing protein reconstitution" Biochimica et Biophysica Acta 1421 (1999), pp. 77-90.

* cited by examiner

Primary Examiner—Michael G. Hartley
(74) Attorney, Agent, or Firm—Calfee, Halter & Griswold LLP

(57) ABSTRACT

The invention provides a drug delivery vehicle for inhalation by a patient. The drug delivery vehicle comprises biocompatible particles between 0.1 and 1.0 microns in diameter, that are loaded with one or more drugs and which are crosslinked together to form agglomerates. The agglomerates can also provide for delivery of contrast-enhancing agents for clinical imaging. The invention also provides methods of making the inventive agglomerates, pharmaceutical compositions comprising the agglomerates, and methods for delivering drugs or contrast-enhancing agents to a patient by inhalation of pharmaceutical compositions containing the agglomerates.

12 Claims, 18 Drawing Sheets

Figure 13

AGGLOMERATED PARTICLES FOR AEROSOL DRUG DELIVERY

CROSS REFERENCE TO RELATED APPLICATION

Figure 1:
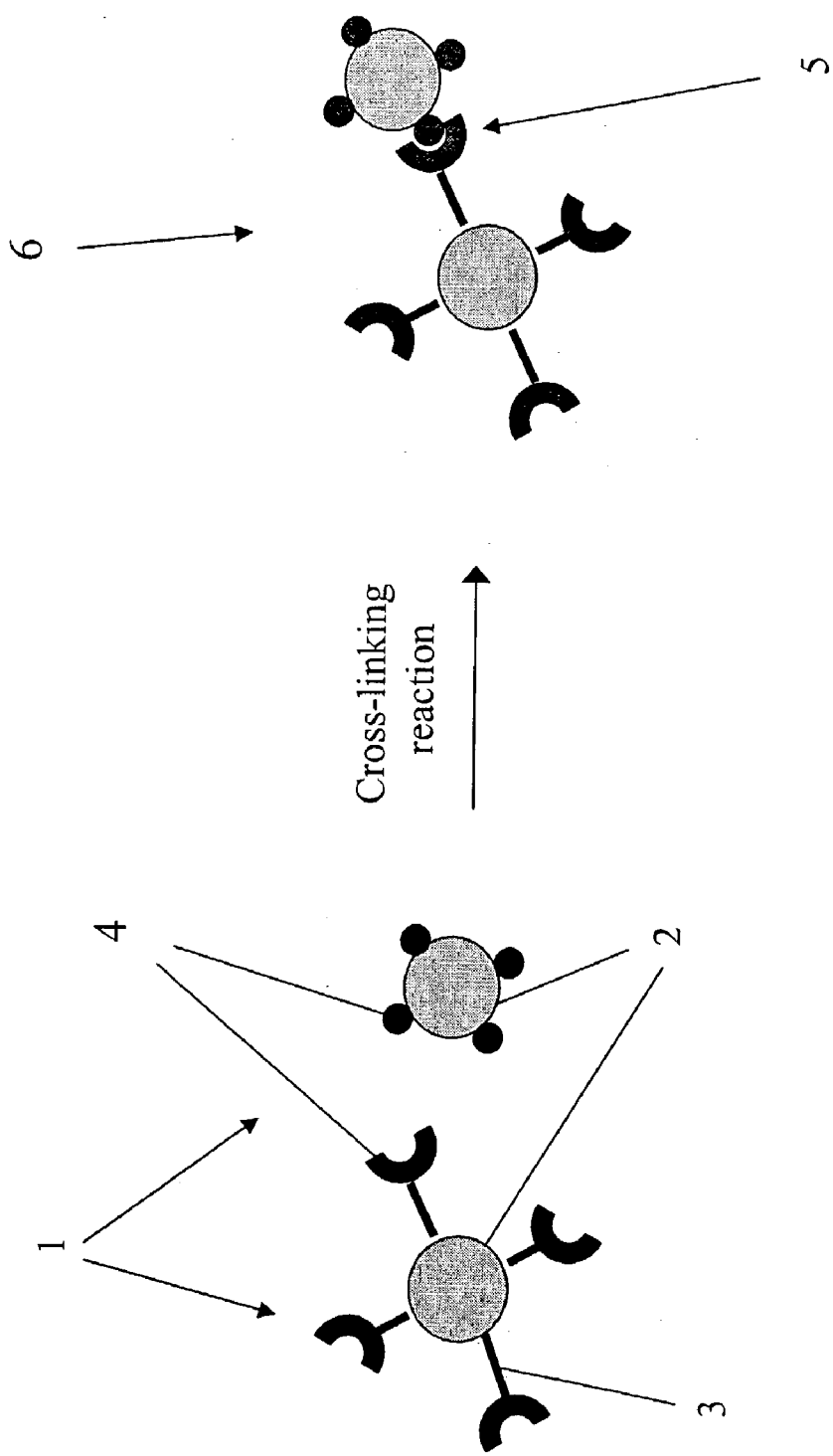

This application claims priority to U.S. Provisional application No. 60/361,961, filed on Mar. 5, 2002, the disclosure of which is incorporated herein in its entirety.

FIELD OF INVENTION

The invention relates to a respiratory drug-delivery vehicle comprising drug-containing particles that are chemically crosslinked together to form agglomerates. The agglomerates are inhaled into the respiratory tract of a patient where the drugs are controllably released from the particles. The invention also relates to methods for making the agglomerates, pharmaceutical compositions containing the agglomerates, and methods for treating patients by delivering such pharmaceutical compositions to a patient.

BACKGROUND

Delivery of drugs to patients, with the goal of having the drugs enter the bloodstream, or of acting locally without entry into the blood, can be performed using a variety of methods. For example, certain drugs are delivered to patients by oral ingestion and enter into the bloodstream though the digestive tract. Oral delivery of drugs, however, has disadvantages. One disadvantage is that there can be extensive metabolism and breakdown of an orally-administered drug in the digestive tract, before it reaches the bloodstream, so that only a fraction of the drug ingested actually reaches the bloodstream. Protein and peptide therapeutics, for example, have very poor stability in the digestive tract and are difficult to administer orally. Another disadvantage of drug delivery by the oral route is that the time required for an ingested drug to enter the bloodstream may be quite long. Finally, ingestion of drugs can cause the patient to experience an upset stomach.

Another method for drug delivery is the parenteral route, also called injection. However, injection is an invasive method of delivery in that the skin of the patient must be punctured. Not only is skin puncture painful to the patient, puncture increases the possibility for infection of the patient by various pathogenic microorganisms. In addition, patients may be reluctant or unable to inject themselves for the purpose of administering a drug.

New routes of drug delivery have emerged which alleviate some of the problems inherent in more traditional drug delivery methods discussed above. Pulmonary or respiratory drug delivery is one new method of drug delivery. In respiratory drug delivery, the drug is inhaled into the lungs of the patient. Inhalation of the drug is accomplished through the use of aerosols or inhalers, for example. Once in the lungs, the drug enters the bloodstream by passage through the lung alveoli. Alternatively, the drug can remain in the respiratory tract and act locally, as in the case of asthma, for example.

Respiratory delivery of drugs has a number of advantages. First, drug delivery by inhalation is not invasive and is very convenient for the patient. Respiratory delivery is suitable for drugs that cannot be delivered orally because many drugs are relatively stable in the lungs. Another advantage of respiratory drug delivery is the tremendous surface area available in the alveoli of the lung, close to 70 square meters per lung, through which the inhaled drug can enter the bloodstream. The result of this large surface area is rapid entry of the drugs into the bloodstream. Drug delivery via the pulmonary route also avoids first pass hepatic and renal effects, common to other modes of drug delivery, which remove the drugs from the body.

Also of importance is that some very important human diseases afflict the respiratory tract, including the lung. Asthma is one such disease. Cystic fibrosis is another such disease. Respiratory delivery of drugs is especially important for these diseases because delivery directly to the respiratory tract allows the drugs to act locally, where the drug effect is needed to alleviate symptoms of the disease. In order to treat such diseases, it is not necessary for the inhaled drugs to enter the systemic circulation.

Although rapid entry of drugs into the bloodstream in respiratory delivery is advantageous, usually little drug is left in the lungs 2–3 hours after inhalation. This can be problematic, especially in cases in which it would be advantageous to slowly release drug into the bloodstream over a period of time, or in cases where it is desired to have the drug remain in the lungs to act locally. To presently achieve slow release, repeated low-level dosing of the drug is required. Heretofore, there has been a lack of success in obtaining inhaled drug formulations that would increase drug residence time in the lung and control the release rate of the drug into the bloodstream. Different formulations of inhaled drugs have been tried in an attempt to solve this problem. However, these formulations, both dry powder and liquid formulations, have not resulted in reproducible increased duration of drug in the lungs, nor extended release of inhaled drugs into the bloodstream, without creating new problems, such as the presence of synthetic polymer or other dry powder excipients in the lung.

The lack of delivery systems resulting in controlled release has been disadvantageous for agents other than drugs. For example, X-ray based imaging techniques (including Computed Tomography or CT) and Magnetic Resonance Imaging (MRI) techniques utilize contrast-enhancing agents. Contrast-enhancing agents are delivered to tissues of the body, are localized therein, and have the effect of differentiating the tissue from surrounding tissues that have not localized the agents when the imaging techniques are used. There are no good delivery systems that result in controlled release of contrast-enhancing agents for imaging.

Therefore, because of the difficulties in achieving long term or controlled release of drugs and contrast-enhancing agents using respiratory delivery, there is a need for inhaled delivery systems that provide controlled release of drugs or contrast-enhancing agents from a reservoir that has been inhaled into the lungs. There is a need for the controlled release of drugs and contrast-enhancing agents from the lungs to be of two types. First, systems that provide a relatively slow and constant rate release from a reservoir of drug inhaled into the lungs are needed. Second, systems that provide variable and controllable rates of drug release from a reservoir of drug in the lungs are needed. In systems that provide for controllable release of drug from the lungs, it would further be desirable if the rate of drug release from the lungs could be controlled even after the drug has been inhaled into the lungs.

SUMMARY OF THE INVENTION

In accordance with the present invention, it has been discovered that controlled release of inhaled drugs can be achieved through the use of chemically crosslinked agglomerates of particles, the particles containing or being associated with drugs. Inhalation of the crosslinked agglomerates of particles by a patient results in delivery of the drugs to the respiratory tract of the patient where the drugs are controllably released from the particles.

Thus, the present invention provides, as a new composition of matter, agglomerates of chemically crosslinked particles, particularly bioresorbable, the particles having an average size of about 0.1 to 1.0 microns in diameter. The particles which preferably are bioserobable or biodegradable also contain or are associated with drugs or other biologically active substances. The rate of release of drugs from the agglomerates is controlled by suitable selection of the nature and density of the chemical crosslinks that hold the particles of the agglomerates together. The rate of release of drugs from the agglomerates is also controlled by cleavage of the chemical crosslinks that hold the particles of the agglomerate together. In another embodiment, the chemically crosslinked agglomerates of particles contain or are associated with contrast-enhancing agents for imaging.

In another aspect, the invention provides pharmaceutical compositions comprising the drug-containing agglomerates or contrast-enhancing agent-containing agglomerates of the present invention. Also provided are pharmaceutical compositions comprising substances that cleave the crosslinks of agglomerates, such compositions being delivered to the respiratory tract of a patient simultaneously with, or subsequently to, inhalation of a pharmaceutical composition of drug- or contrast-enhancing agent-containing agglomerates. The purpose of the substances that cleave agglomerate crosslinks is to control the rate of drug or contrast-enhancing agent release from the particles of the agglomerates. Also provided are pharmaceutical compositions comprising both drug-containing agglomerates and crosslink-cleaving substances or comprising both contrast-enhancing agent-containing agglomerates and crosslink-cleaving substances.

In still another aspect, the invention provides methods for treating patients by delivery to the respiratory tract, of pharmaceutical compositions comprising the drug-containing agglomerates, compositions comprising the crosslink-cleaving substances, or compositions comprising both the agglomerates and the crosslink-cleaving substances.

In another embodiment, the invention provides methods for administering pharmaceutical compositions comprising contrast-enhancing agents for subsequent imaging of cells, tissues, organs or parts of the body.

BRIEF DESCRIPTION OF THE DRAWINGS

The present invention may be more readily understood by reference to the following drawings wherein:

FIG. 1 is a schematic diagram illustrating formation of a chemical crosslink between two reacting particles;

FIG. 2 is a schematic diagram illustrating formation of a chemical crosslink between two reacting particles by reaction with a spacer molecule;

FIG. 3 is a schematic diagram illustrating formation of chemical crosslinks between multiple reacting particles to form a crosslinked agglomerate;

FIG. 4 is a schematic diagram illustrating partial cleavage of crosslinks of an agglomerate;

FIG. 5 shows the size distribution of COOH liposomes and NH2 liposomes as measured by dynamic light scattering;

FIG. 6 shows the size distribution of agglomerates of liposomes formed using S-EGS, and of unagglomerated liposomes, as measured by Fraunhofer diffraction;

FIG. 7 shows the aerodynamic diameter, as measured with a cascade impactor, of agglomerated and unagglomerated insulin-containing liposomes;

FIG. 8 shows the rate of release of insulin from agglomerated and reassembled liposomes;

FIG. 9 shows cleavage of the S-EGS crosslinks of liposome agglomerates by hydroxylamine;

FIG. 10 shows the theoretical encapsulation efficiency of 75 mM liposomes compared to experimental data of insulin-loaded liposomes;

FIG. 11 shows comparison of size distribution by Fraunhofer diffraction of liposomes (37.5 mM lipid) agglomerated with 50.43 mg/ml of DMS and analyzed after 1 day with unagglomerated liposomes;

FIG. 12 shows comparison of size distribution by Fraunhofer diffraction of liposomes (75 mM lipid) agglomerated with 150.832 mg/ml of DTBP and analyzed after 1 day with unagglomerated liposomes;

FIG. 13 shows aerodynamic characterization of unagglomerted and DTBP-agglomerated liposomes containing insulin using a cascade impactor;

FIG. 14 shows loss of loaded insulin upon nebulization for different liposomal formulations;

FIG. 15 shows comparison of size distribution, by Fraunhofer diffraction, of liposomes encapsulating insulin (37.5 mM lipid) agglomerated with 45.86 mg/ml of DTBP with cleaved agglomerates (for the cleavage, 0.7 ml of the agglomerates were diluted to 1.42 ml with citrate buffer and cleaved with 4.93 mg/ml of DTT at 37° C. for 2 or 4 hours);

FIG. 16 shows release of insulin from parent liposomes and sulfo-EGS-agglomerates followed by cleavage (using hydroxylamine);

FIG. 17 shows release of insulin from parent liposomes and sulfo-EGS-agglomerates followed by multi-cleavage (using hydroxylamine); and FIG. 18 shows release of ciprofloxacin from DTBP-agglomerates followed by cleavage using DTT.

DETAILED DESCRIPTION OF THE INVENTION

Definitions

Unless otherwise indicated, the following terms used in this document have the following meanings:

"Particle" refers to any, roughly spherically-shaped object.

"Crosslink" refers to a covalent chemical linkage or connection that attaches two particles to one another.

"Cleaver" refers to substances that break or cleave crosslinks.

"Tether" refers to a molecule which attaches a reactive chemical group to the surface of a particle.

"Spacer" refers to a molecule containing multiple reactive chemical groups, each of which is capable of reacting with a reactive chemical group attached to the surface of a particle.

"Reactive particles" refers to particles that have reactive chemical groups attached to their surface, are capable of becoming crosslinked to one another, but have not yet done so.

"Agglomerate" refers to multiple particles attached to one another by chemical crosslinks.

"Drug" refers to any substance that, when administered to or taken into the body of a human or animal patient, may modify one or more of the functions of the body.

"Respiratory drug" refers to a drug which is delivered, or intended to be delivered, to a patient by inhalation into the patient's respiratory tract.

"Contrast-enhancing agent" refers to any substance that, when administered to or taken into the body of a human or animal patient, and localized within cells, tissues or organs, may enhance or differentiate those cells, tissues or organs from cells, tissues or organs that have not localized the agent when imaging techniques are used to examine the cells, tissues or organs.

"Loading" refers to methods used to associate drugs with, attach drugs to, or encapsulate drugs into, particles or agglomerates.

"Pharmaceutical composition" refers to an aggregation of ingredients, generally including a drug, or a contrast-enhancing agent, that is intended for administration to a patient.

"Therapeutically effective" amount refers to an amount of drug or pharmaceutical composition of drug needed to achieve a desired therapeutic result.

"Drug delivery vehicle" refers to the components of a pharmaceutical composition which allow or facilitate delivery of drugs in the composition into the body of a patient.

"Contrast-enhancing agent vehicle" refers to the components of a pharmaceutical composition which facilitate delivery of contrast-enhancing agents in the composition into the body of a patient.

"Controlled release" refers to the ability to control the rate at which a drug in a pharmaceutical composition of the present invention is released from its delivery vehicle under physiological conditions, such as when the drug delivery vehicle is in the lung of a patient.

In accordance with the present invention, it has been found that respiratory drugs and contrast-enhancing agents can be made to exhibit controlled release characteristics by using as a drug delivery vehicle, pharmaceutical compositions containing drug-loaded agglomerates formed from crosslinked particles having an average size of about 0.1 to 1.0 microns in diameter. In particular, it has been found that the rate at which a respiratory drug is released from the drug delivery vehicle inside the patient's respiratory tract can be effectively controlled by suitable selection of the nature and density of the crosslinks that attach the particles together to form the agglomerates, as well as the size and number of particles forming the agglomerates.

The present invention may be more readily understood by reference to FIGS. 1, 2, 3 and 4. Referring now to the drawings and particularly to FIG. 1, a schematic diagram illustrating formation of a chemical crosslink between two reacting particles 1 is shown. The reacting particle 1 to the left, comprises a particle 2, multiple tether molecules 3, and multiple reactive chemical groups 4 attached to the tethers 3. The reacting particle 1 to the right, comprises a particle 2 and multiple reactive chemical groups 4. The reacting particle 1 to the right does not have tethers 3. As shown, reactive chemical groups 4 can be attached to a particle 2 by a tether 3, as shown on the left, or can be directly attached to the particle 2, as shown on the right. A reactive chemical group 4 attached to the surface of each of the reacting particles 1 undergoes a chemical reaction such one or more crosslinks 5 are formed. The crosslinked particles form an agglomerate 6, as shown here, comprising two crosslinked particles.

Figure 2:
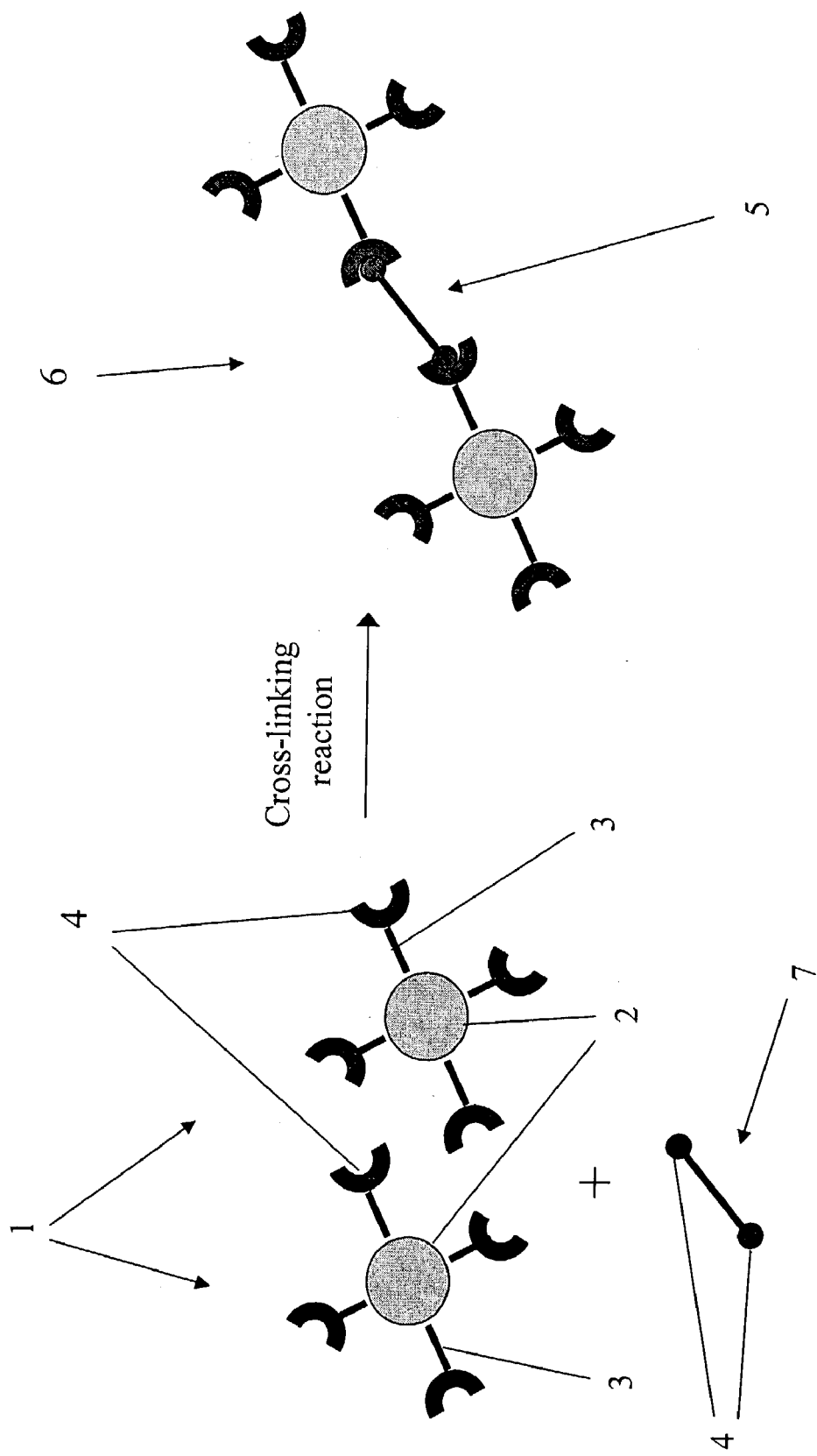

Referring now to FIG. 2, a schematic diagram illustrating formation of a chemical crosslink between two particles by reaction with a spacer molecule is shown. Two reacting particles 1 are shown, both of which comprise a particle 2, multiple tethers 3 and multiple reactive chemical groups 4 attached to the tethers 3. Also shown is a spacer molecule 7, which has at least two reactive chemical groups 4. As shown, a reactive chemical group 4, that is part of each reacting particle 1, undergoes a chemical reaction with different reactive groups 4 that are part of the spacer 7. A crosslink 5 is formed between the two reacting particles 1. The crosslinked particles form an agglomerate 6, as shown here, comprising two crosslinked particles.

Figure 3:
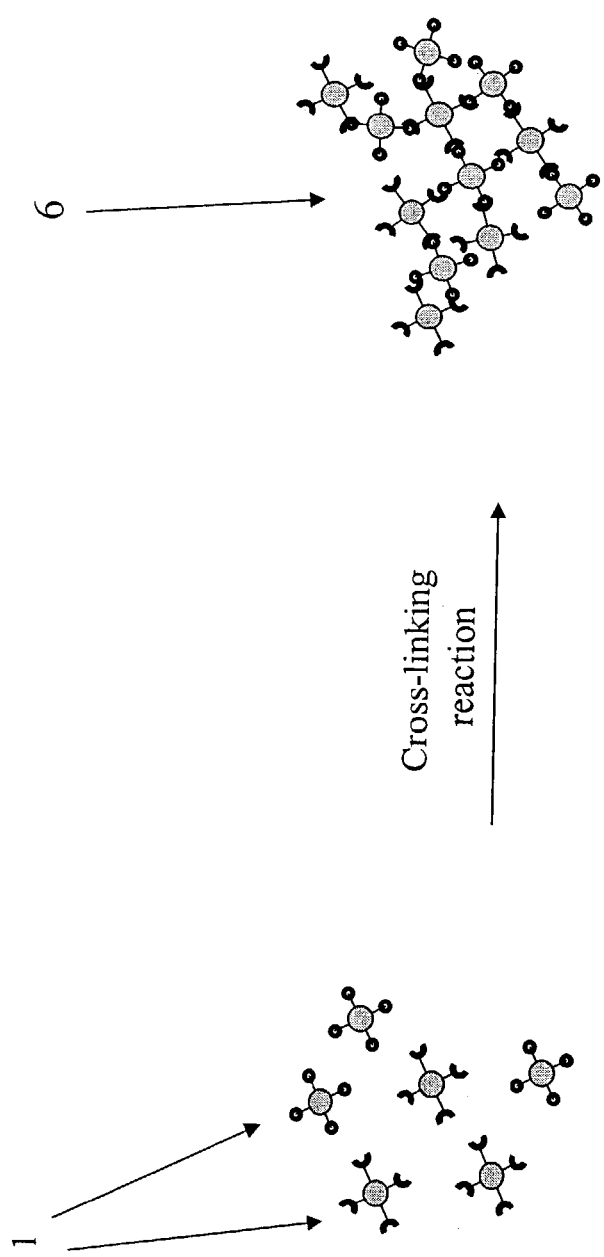

Referring now to FIG. 3, a schematic diagram illustrating formation of chemical crosslinks between multiple reacting particles to form a crosslinked agglomerate is shown. The diagram illustrates multiple reacting particles 1 that undergo chemical reactions to form an agglomerate 6. The diagram extends what is shown in FIGS. 1 and 2 to show that agglomerates 6 can contain multiple crosslinked particles. The agglomerate 6 has crosslinked particles in three dimensions, not just the two dimensions shown in FIG. 3. The diagram also illustrates that multiple of the reactive groups attached to the surface of a single reacting particle can undergo chemical reactions to produce an agglomerate where each reacting particle is attached to multiple other reacting particles.

Figure 4:
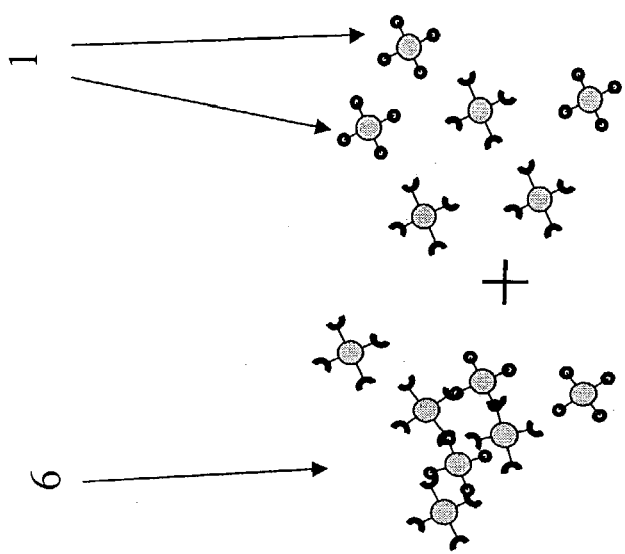
Figure 4:
Figure 4:
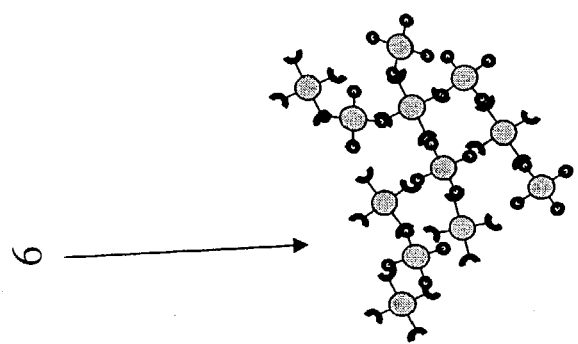

Referring now to FIG. 4, a schematic diagram illustrating cleavage of crosslinks of an agglomerate is shown. The diagram shows an agglomerate 6, on the left side of the arrow labeled "cleavage." The arrow represents breakage or cleavage of some of the crosslinks that hold the reactive particles of the agglomerate 6 together. The result of cleavage of crosslinks is shown on the right side of the arrow labeled "cleavage." Shown on the right are individual reactive particles 1 that have undergone cleavage of their crosslinks. The agglomerate 6 shown on the right side of the arrow represents the original agglomerate, less the reactive particles that have undergone crosslink cleavage. The cleavage reaction represented here schematically, represents one way in which drugs that are carried by agglomerates are released within the respiratory tract of a patient to which the drug-containing agglomerates have been delivered.

Particles

The particles used to form the agglomerates of the present invention are made of any of a number of biocompatible materials. Biocompatible materials are those that are not toxic to the body of a patient when delivered therein. Such materials are preferably organic and can be polymeric or nonpolymeric. Some examples of such materials are lipids and biodegradable polymers, or combinations of these. Such biodegradable polymers include, for example, a polymer from the linear polyester family, such as polylactic acid, polyglycolic acid or polycaprolactone and their associated copolymers (e.g. poly (lactide-coglycolide) at all lactide to glycolide ratios and both L-lactide or (D,L lactice). Polymers such as polyorthoester, polyanhydride, polydioxanone and polyhyroxybutyrate may also be employed. The particles are preferably between 0.1 and 1.0 microns in diameter. Such biocompatible particles are preferably also biodegradable. Biodegradability means that the particles are eventually broken down or decomposed in the body and any remnants of the particles are dissipated or removed from the body. This is advantageous in that there is no buildup of particles over time in the respiratory tract of the patient.

In one embodiment, liposomes are used as the particles to form the agglomerates. A variety of different types of liposomes are well known in the art. Generally, liposomes are spherical particles containing an internal cavity. The walls of liposomes generally are comprised of a bilayer of lipids, particularly phospholipids. There are numerous lipids and phospholipids that can be used to make liposomes. These lipids and phospholipids are also well known in the art. Many of the types of liposomes, as well as the lipids and phospholipids, are described in references such as U.S. Pat. No. 5,049,389, issued to R. Radhakrishnan, and Storm and Crommelin, 1998, Pharmaceutical Science and Technology Today, 1:19–31, the descriptions being herein incorporated in their entirety by reference. The liposomes of the present invention preferably have a lipid composition that is similar to the lipid composition of surfactants in the lungs of an individual.

The liposomes of the present invention may be prepared by any of the standard methods known in the art for making liposomes. A variety of such methods are known. Some such methods include hydration of dried lipids, introduction of a volatile organic solution of lipids into an aqueous solution causing evaporation of the organic solution, and dialysis of an aqueous solution of lipids and detergents or surfactants to remove the detergents or surfactants. Many of these methods are described in U.S. Pat. No. 5,049,389, Storm and Crommelin, 1998, Pharmaceutical Science and Technology Today, 1:19–31, and Szoka and Papahadjopoulos, 1978, Proc Natl Acad Sci USA, 75:4194–8, the descriptions of which are incorporated herein in their entirety by reference.

After liposomes are made, there are techniques well known in the art for manipulating the liposomes that can also be used in practice of the present invention. For example, a preparation of liposomes made by standard techniques may vary in size and lamellarity (i.e., wall thickness) after it is made. Techniques such as subjecting the liposomes to a high shearing force, extrusion of the liposomes through membranes, or sonication of the liposomes can be used either to select liposomes of a desired size or modify the liposomes such that they have a desired size. After manipulation of liposomes by these methods, the size distribution of the liposomes can be measured to ensure that liposomes of the desired size have been obtained. Techniques well known in the art, such as Fraunhofer diffraction and dynamic light scattering (DLS) are used to measure the size distribution of the liposomes. Such techniques measure an equivalent spherical diameter which, in the case of Fraunhofer diffraction, is the diameter of a sphere with the same light scattering properties as the measured liposomes. In the case of DLS, equivalent spherical diameter is the diameter of a sphere with the same diffusion coefficient as the measured liposomes.

In another embodiment, particles made of biocompatible polymers are used as the particles of the agglomerates. Such particles can be either solid or hollow, can have various densities, are roughly spherical with a diameter in the range of about 1 to 500 nm. Many such particles that can be used in the agglomerates of the present invention can be purchased commercially. For example, Bangs Laboratories, Inc. (Fishers, Ind.) sells many such particles.

The particles of the present invention have reactive chemical groups attached to their surface. Such attachment can be direct or by a tether.

Particles are Associated with Drugs or Contrast-Enhancing Agents

The particles of the present invention contain drugs, are attached to drugs, or are associated with drugs such that the drugs are delivered to the respiratory tract of a patient upon inhalation of a pharmaceutical composition containing the agglomerates. Such particles are said to be "loaded" with drugs. The methods whereby the particles become loaded with drugs is referred to as "loading."

Drugs that are contemplated for delivery by the agglomerates of the present invention include insulin, ciprofloxacin, leuprolide, tobramycin, cyclosporin, interferon, antitrypsin, protease inhibitors, deoxyribonucleases, recombinant adenoviruses, and others (see Adjei and Gupta, 1997, Inhalation delivery of therapeutic peptides and proteins, Marcel Dekker Inc., New York).

Especially preferred drugs for use in the present invention are respiratory drugs. Such respiratory drugs may be those that are designed to treat diseases or afflictions of the respiratory tract, including the lungs, for example. One particularly good example of such a disease is asthma. Drugs that are advantageously delivered using the present invention, for example, may be those that function particularly well when delivered to a patient by the respiratory route, or may be drugs that are difficult or impossible to deliver to the patient by any other route of delivery.

Contrast-enhancing agents can also be loaded into the particles that are used to form the agglomerates of the present invention. Agglomerates containing contrast-enhancing agents are useful in imaging techniques, such as CT, MRI and others. Typical contrast-enhancing agents used in CT include a variety of iodinated compounds, such as iohexol and iodixanol, both nonionic compounds, and hexabrix, an ionic compound. Other contrast-enhancing agents are used in CT and can also be used in agglomerates. Typical contrast-enhancing agents used in MRI include gadolinium and dysprosium. Other contrast-enhancing agents used in MRI include iron particles and others. Any of these agents can be used in the agglomerates of the present invention. In addition, an agglomerate preparation may contain more than one contrast-enhancing agent. In one case, an agglomerate contains a contrast-enhancing agent for use in CT and a separate contrast-enhancing agent for use in MRI, providing a composition that enhances contrast in imaging with both CT and MRI.

In addition, an agglomerate may contain one or more drugs in addition to one or more contrast-enhancing agents. Such an agglomerate is useful to track or follow the movement or disbursement of the drug in the body after delivery.

It should be noted that the invention contains no limitation on when in the process of making agglomerates, loading of the particles with drugs is performed. For example, loading may be performed before the reactive particles are crosslinked together to form agglomerates. Alternatively, loading may be performed after the particles have been crosslinked together to form agglomerates.

When liposomes are used as the particles of the invention, there are a variety of methods known in the art for loading drugs into the liposomes. Generally, drugs which are hydrophilic in nature are located or associated with the internal cavity of the liposome particles. Drugs which are lipophilic in nature generally are located or associated with the lipid bilayer of liposome particles. In passive loading, liposomes are formed in a solution of the drug to be used. In active loading, a variety of methods are known in the art. In one type of active loading, called pH based loading, a proton is dissociated from the drug molecules, causing the drugs to enter into and remain in the liposomes (Ceh and Lasic, 1997, J Colloid Interface Sci, 185:9–18.). In another type of active loading, called ammonium sulfate loading, the drug is caused to enter into liposomes due to presence of an ammonium sulfate gradient (Ceh and Lasic, 1997, J Colloid Interface Sci, 185:9–18.). In still another method, a chelating agent within the liposome results in trapping of drug therein as well as further diffusion of drug into the liposomes (Patent No. WO0023052 by Colbern, Working and Slater, entitled "Liposome-Entrapped Topoisomerase Inhibitors"). The above techniques are also used to load drugs into polymeric particles.

After the loading of drug into particles, steps may be used to remove drug that has not been loaded and is not associated with particles. Such steps may comprise techniques such as ion exchange, diafiltration, or washing of the particles or agglomerates using ultracentrifugation.

Crosslinks

The reactive particles of the present invention are crosslinked together to form agglomerates. The crosslinking occurs when covalent chemical bonds form between reactive chemical groups that are attached to separate reactive particles, or when covalent chemical bonds form between reactive particles and the reactive chemical groups that are part of a spacer molecule. There are a variety of reactive chemical groups that can be used. Some examples are —$NH_2$, —COOH and —SH. It is not a requirement that the reactive chemical groups that react with one another be identical. The reactive chemical groups that react with one another can be different. However, the reactive chemical groups of the present invention react with one another to form covalent chemical bonds. Preferably, the crosslinks of the invention are biocompatible and non-toxic to the patient.

In one embodiment, the reactive chemical groups can be directly attached to the surface of the reactive particles. In another embodiment, the reactive chemical groups can be attached to the particles by tether molecules. One such tether molecule is polyethylene glycol (PEG). It is not a requirement that reactive chemical groups, that react with one another, be attached to reactive particles in the same way. For example, it may be that a reactive chemical group directly attached to a reactive particle, reacts with a reactive chemical group that is attached to another particle by a tether molecule. However, it may be that reactive chemical groups that react with one another are attached to the reactive particles in the same way, either directly attached or attached through a tether molecule. The reactive chemical groups may be attached to the particles during the process of making the particles or can be attached to the particles after the particles are made. Also, the reactive chemical groups may be attached to the particles before, during or after the particles are loaded with drugs. Certain particles of the present invention that already have chemically reactive groups attached to their surface can be purchased commercially.

In addition to reaction of reactive chemical groups directly with each other to form crosslinks, spacer molecules can be used to crosslink reactive particles to one another. Spacers may comprise linear molecules or branched molecules. Spacers are preferably 1 to 500 nm in length. Spacer molecules contain at least two reactive chemical groups.

It should also be realized that through the use of different chemical crosslinks and different spacer molecules, it is possible to change the distance between crosslinked particles within an agglomerate. For example, in agglomerates that contain crosslinks where no spacer molecules have been used, particles within the agglomerate may be, on average, a relatively close distance to one another within the agglomerate. In agglomerates that contain crosslinks where spacer molecules have been used to form the crosslinks, particles within the agglomerate may be, on average, a relatively farther distance from one another within the agglomerate. Selection of different crosslinks in this way is a method to alter the density and, therefore, control the rate at which drugs are released from an agglomerate. For example, in agglomerates in which particles are relatively close to one another (i.e., of high density), the rate of drug release is relatively slow. In agglomerates in which particles are relative far from one another (i.e., of low density), the rate of drug release is relatively rapid.

Some different embodiments of the crosslinking chemistry are described below. Crosslinking that does not utilize a spacer molecule is exemplified by the chemical reaction shown below which uses 1-ethyl-3-(3-dimethylaminopropyl) carbodiimide, also called EDC, to initiate the crosslinking reaction between links on different particles. In the chemical reaction shown below, the $R_1$ group in compound I represents a particle and the attached —COOH group represents a link attached to the surface of the particle. The $R_2$ group in compound IV represents a second particle and the attached —$NH_2$ group represents a link attached to the surface of that particle. Reaction of EDC (compound II) with compound I results in the formation of compound III as a reaction intermediate. As shown below, the $R_1$ particle is attached to EDC in the compound III reaction intermediate (i.e., the $R_1$—COO group with the box around it). Reaction of compound IV, containing the second particle, with compound III results in formation of compound V, which represents the crosslinked particles $R_1$ and $R_2$.

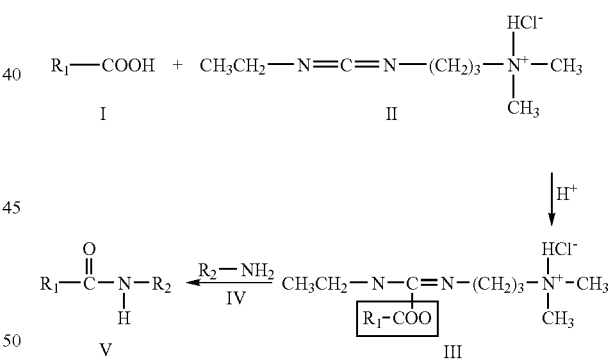

Crosslinking that utilizes a spacer molecule is exemplified by the chemical reaction shown below which uses sulfo-[ethylene glycobis(succinimidylsuccinate)], also called S-EGS, as the spacer molecule. In the chemical reaction shown below, compound I represents a molecule of S-EGS. Compound II represents two separate molecules of R—$NH_2$. Each R group therein represents a particle. Each particle has an —$NH_2$ group attached to its surface. Reaction of the —$NH_2$ groups attached to the particles with the S-EGS results in formation of compound III. Compound III represents the crosslinked particles and shows the R particles and —NH links which have been crosslinked by the S-EGS. Note that the carbon-oxygen backbone of the S-EGS molecule remains as a part of the crosslink of the agglomerate.

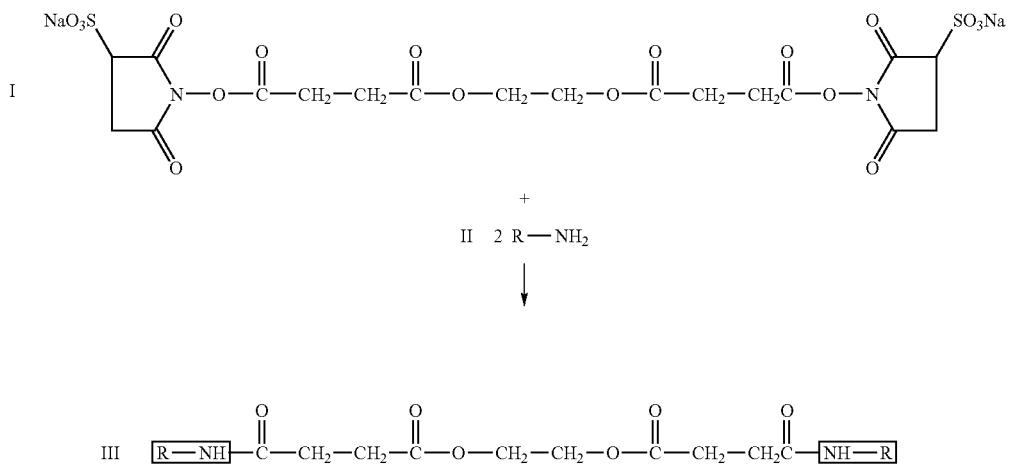

It should be noted that, in addition to the above two reactions, there are many other types of chemistries that can be used to crosslink particles together to form agglomerates. A variety of different reactive chemical groups can be used. In addition to the —COOH and —NH$_2$ links described above, some other reactive chemical groups are —CHO, SO$_4$—, and the succinimide ester. It should be noted that the particular types of reactive chemical groups, as well as how they are attached to the particles, may depend on the particular particles used to form the agglomerates. In addition, a variety of different spacers are possible. Some other spacers are polyethylene glycol, polyethylene oxide, and polypropylene oxide chains.

It should also be understood that the extent of the crosslinking reactions can be limited or stopped to control the size of agglomerates or to allow making of agglomerates that have various layers, as is described below. Various means exist for limiting or stopping the chemical reactions that result in formation of the crosslinks. One such means is to limit the amount of one or more reactants. Other such means exist to limit or stop such chemical crosslinking reactions. Such means are well known to those skilled in the art of chemistry.

It should also be noted that crosslinks of the present invention can be either cleavable or non-cleavable (i.e., permanent). Cleavable crosslinks are those that can be broken (i.e., one of the covalent chemical bonds that attaches two particles to one another is destroyed), preferably by addition of chemical substances, herein called "cleavers." When cleavable crosslinks of an agglomerate are cleaved, particles become detached from the agglomerate and, preferably, the rate at which drug is released from the detached particle is altered. It is well known in the field that the diffusion rate of drug out of particles is proportional to the exposed surface area, and therefore an increased surface area would lead to increased release rate of drug. Cleavage of a cleavable crosslink by a cleaver substance is specific in that a given cleaver substance will not cleave all types of crosslinks. Preferably, a given cleaver substance is specific for one or a few different crosslinks. Non-cleavable crosslinks are those for which no cleaver substances exist or are those which cannot be broken. Cleaver substances can function either by breaking covalent chemical bonds within tether molecules or within spacer molecules. Preferably, cleaver substances break covalent bonds within spacer molecules.

In addition, cleavable crosslinks can be either naturally cleavable or inducibly cleavable. Naturally cleavable crosslinks are those that are cleaved in the respiratory tract after administration of agglomerates to a patient, the cleavage being caused by substances normally present within the respiratory tract of individuals. Therefore, there are cleavers normally present within the respiratory tract of individuals that are able to cleave certain crosslinks, such crosslinks being called naturally cleavable crosslinks. In this instance, cleavage of the naturally cleavable crosslinks of the agglomerate occurs without administration of exogenous cleavers to the patient. The invention does not exclude that additional cleavers can be exogenously administered to a patient. Such cleavers can be administered to a patient simultaneously or concurrently with the agglomerates. Such cleavers can also be administered to a patient subsequent to administration of the agglomerates.

In one example, particles are crosslinked to form agglomerates using a dithiobenzyl (DTB) urethane linkage. Such a linkage carries a disulfide bond that is cleaved by free thiols. While there are low levels of cysteine and glutathione in the lung, capable of causing some cleavage of disulfide bonds between particles, further addition of a free thiol as a "cleaver" dose triggers the accelerated release of the drug by cleavage of the links holding particles together and liberation of free particles from the agglomerate.

In one example for crosslinking agglomerages, which is cleavable by free thiols, methoxypoly(ethyleneglycol)-Distearoylphosphatidylethanolamine (mPEG-DSPE) conjugate containing o- or p-dithiobenzyl carbamate (DTB-urethane) linkage moiety is used. The chemical linkage and its cleavage by a thiol is shown below. The DTB-urethane linkage is located between the lipid (DSPE) and the mPEG as shown below. This disulphide-linked conjugate is cleavable with cysteine resulting in regeneration of phosphatidylethanolamine lipid in its natural form.

Crosslinks that are inducibly cleavable are those for which there are no cleaver substances that are normally present within the respiratory tract that can cleave crosslinks. In order to cleave inducibly cleavable crosslinks, cleaver substances must be administered exogenously to the patient so that they contact the crosslinks of the agglomerates already in the respiratory tract of the patient. Alternatively, inducibly cleavable crosslinks can be cleaved by cleaver substances mixed in with the agglomerates and administered to the patient at the same time that the agglomerates are administered. One example of an inducibly cleavable crosslink is the crosslink formed by the S-EGS spacer in compound III above. This crosslink is cleavable by hydroxylamine. Another example of an inducibly cleavable crosslink is a crosslink that is cleaved by thiol compounds, for example. Other examples are hydrolysable crosslinks.

The usefulness of chemical substances such as cleavers is that they can be used to control the rate at which agglomerates release their associated drugs. For example, by cleaving crosslinks, agglomerates can increase the rate at which associated drugs are released. Individual particles may or may not be released from the agglomerates as a result of cleavage of the crosslinks. Substances that control the rate at which agglomerates release their associated drugs by mechanisms other that cleavage of crosslinks are contemplated. For example, one such chemical substance may cause release of drug from a particle by dissolution of liposomes or polymeric particles of agglomerates, for example.

Agglomerates

The agglomerates of the present invention comprise at least two reactive particles that are crosslinked together. Preferably, an agglomerate comprises between ten and several thousand particles that are crosslinked together. The dimensions of the agglomerates are such that the agglomerates are preferably greater than one particle thick in each of three dimensions, but may be as much as 300 particles thick in any dimension. The agglomerates may have roughly similar thickness or length in each of three dimensions. Agglomerates are generally between 10 and 50 microns in length in any dimension.

The agglomerates of the present invention are also defined by their aerodynamic diameter. As described by Edwards, et. al. in U.S. Pat. Nos. 5,874,064 and 6,254,854 B1, the property of "aerodynamic diameter" can be used to determine whether an object (e.g., agglomerate) can be inhaled into the alveoli of the lung. Aerodynamic diameter ($d_{aer}$) is defined as:

$$d_{aer} = d\sqrt{\rho}$$

where d is the geometric diameter of the agglomerates and $\rho$ is the specific gravity. As stated in the Edwards' patents, maximal deposition (approximately 60%) of objects in an aerosol in the alveoli of the lung is obtained at $d_{aer}$=3 microns. Acceptable $d_{aer}$ for the agglomerates of the present invention are preferably from 1 to 10 microns, more preferably from 2 to 7 microns, most preferably from 2 to 5 microns. In the case where it is not desirable to deliver drugs to the lung alveoli, $d_{aer}$ for the agglomerates may be outside of these ranges of values. For example, for agglomerates to reach the lung, but not the alveoli of the lung, $d_{aer}$ may be as large as 10–15 microns.

Aerodynamic diameter of agglomerates is measured by the use of a cascade impactor. Cascade impactors consist of an interconnected series of tubes of decreasing diameters, and a deposition surface (e.g., a slide or plate) located at the point where each tube connects to the next tube of a smaller diameter. An aerosol containing the agglomerates is drawn into the tube of the largest diameter at a constant volumetric rate. Because the aerosol moves through the instrument at constant volume, as the aerosol progresses to each smaller tube, the speed at which the aerosol moves through the tubes increases. The agglomerates of highest $d_{aer}$ in the aerosol impact onto the deposition surface associated located at the end of the first tube which is the tube with the largest diameter. Agglomerates of progressively lower $d_{aer}$ impact on succeeding deposition surfaces. After the aerosol has finished moving through the instrument, the deposition surfaces are removed from the instrument and the agglomerates deposited onto the various deposition surfaces are removed and counted. Because the instrument has been previously calibrated, using aerosols containing objects of known $d_{aer}$, the relationship between $d_{aer}$ and the particular deposition surface onto which a particle deposits is known. Using this relationship, the $d_{aer}$ distribution of agglomerates in an aerosol is determined. The use of cascade impactors to determine $d_{aer}$ of objects in an aerosol is well known in the art. One well-known source of cascade impactors is Andersen Instruments.

An important aspect of the agglomerates is that an individual particle that becomes part of an agglomerate is attached to at least one other particle, preferably more than one other particle, through the crosslinks that are formed. Attachment of a particle to more than one other particle is possible because particles used in the present invention preferably have numerous reactive chemical groups attached to their surface. These reactive chemical groups preferably cover the entire surface of the spherical or roughly-spherical particles. Preferably, most or all of these reactive chemical groups are capable of forming crosslinks with reactive chemical groups present on the surface of other particles, or with spacers.

It should be apparent, however, that it is not a requirement that every particle that is part of an agglomerate form crosslinks with more than one other particle. Particles located on the exterior surface of an agglomerate may form crosslinks with only one other particle. It should also be apparent that not every reactive chemical group located on the surface of a particle that is capable of forming crosslinks with other reactive chemical groups necessarily does so. Some, or even many, reactive chemical groups, located on the surface of a particle may not form crosslinks, even though the particle is part of an agglomerate and attached to more than one other particle.

It is an important aspect of the invention that agglomerates can be made that have different densities of crosslinking. As an illustrative example, consider a reactive particle that has 100 reactive chemical groups on its surface. A multiplicity of such particles are reacted together to form two different agglomerates. In the first agglomerate, 80 out of the 100 available reactive groups on the surface of each particle form crosslinks. In the second agglomerate, 30 out of the 100 available reactive groups on the surface of each particle form crosslinks. It can be said that the first agglomerate has a higher density of crosslinks than does the second agglomerate. Differences in density of agglomerates is one way in which the rate of drug release from an agglomerate is controlled.

It is also an important aspect of the invention that agglomerates can be made that contain both cleavable and non-cleavable crosslinks. The cleavable crosslinks can be one or both of naturally cleavable and inducibly cleavable crosslinks. Also, the relative proportion of cleavable relative to non-cleavable crosslinks can vary. For example, the proportion of non-cleavable crosslinks in an agglomerate can be increased relative to the proportion of cleavable crosslinks for the purpose of slowing the rate at which drugs are released from the agglomerates.

In addition to these variations in the crosslinks that hold the particles of an agglomerate together (e.g., density of crosslinks, proportion of cleavable versus non-cleavable crosslinks, etc.), a single agglomerate can be comprised of different types of particles. For example, agglomerates can be made that comprise both particles that are loaded with drugs and particles that are not loaded with drugs. Agglomerates could also be made of two or more particle types, each particle type being loaded with a different drug or different concentrations of the same drug. An agglomerate can also be made that has particles that contain drug and other particles that are loaded with other substances, such as cleavers for example.

It is also an important aspect of the present invention that agglomerates comprised of different "layers" of particles, crosslinks, or both are contemplated. An illustrative example is an agglomerate that is roughly spherical and is approximately 100 particles thick or has a diameter of 100 particles. Consider such an agglomerate to have two layers. The first layer includes the center of the roughly spherical agglomerate and all particles of the agglomerate that are within a diameter of 50 particles from the center of the agglomerate. The second layer of such an agglomerate includes all particles that are farther than a distance of 50 particles from the center of the agglomerate. This second layer of the agglomerate comprises a shell of the outermost 50 particles of the agglomerate. Now consider that each of the two layers of such an agglomerate is different. For example, the particles comprising the first layer are loaded with drug and the particles comprising the second layer are not loaded with drug. Another example is that the particles comprising the first layer are attached to one another by cleavable crosslinks while the particles comprising the second layer are attached to one another by non-cleavable crosslinks. Still another example is that the particles comprising the first layer of the agglomerate are attached to one another by crosslinks that are of a relatively high density while the particles comprising the second layer of the agglomerate are attached to one another by crosslinks that are of a relatively lower density. Other differences between the layers of such an agglomerate, based on particles, crosslinks, drugs, any combination of these or other components of the agglomerates can be easily contemplated. Further, it is not a limitation of such agglomerates that there are only two layers. Agglomerates that have more than two layers, between 2 and 10 layers, between 10 and 50 layers, or even more than 50 layers are contemplated. Design of agglomerates with such "layering" is a way to make agglomerates that release drugs therefrom in a controlled manner.

Pharmaceutical Compositions

Preferably, the agglomerates are in a composition that can be inhaled into the lungs of the patient. Because the particles that comprise the agglomerates are loaded with one or more drugs, the agglomerates are used to administer drugs to the respiratory tract of a patient after inhalation. In one embodiment, the agglomerates are inhaled into the alveoli of the lung in order that drugs delivered by the agglomerates can enter into the bloodstream of the patient.

In order for the agglomerates of the present invention to be inhaled into the respiratory tract, the agglomerates are preferably part of a pharmaceutical composition which is administered to a patient. Such pharmaceutical compositions are preferably an aqueous suspension, however the agglomerates can also be dried. Drying of agglomerates which comprise liposomes uses substances such as sugars, glucose, trehalose and rafinose for example, to stabilize the lipid bilayer. The preferred method for drying the agglomerates is freeze drying. Another method for drying the agglomerates is spray drying. Both methods are well known to those of skill in the art.

Methods for making such pharmacuetical compositions are known in the art. One reference for making pharmacuetical compositions is Remington's Pharmaceutical Sciences, Mack Publishing Co., Easton, Pa.

Administration of the Pharmaceutical Compositions

The pharmaceutical compositions of the present invention are administered to human or animal patients, preferably by the respiratory route. The formulations administered by the respiratory route are generally oral aerosol formulations. Such formulations can be administered via the respiratory route in a variety of ways.

One widely used method for dispensing such an aerosol drug formulation involves making a formulation of the drug in a liquefied gas known as a propellant. The drug may be dissolved or suspended in the propellant, or in a combination slurry-solution. The formulation is dispensed by actuation of a dose metering valve affixed to the container the valve being designed to consistently release a fixed, predetermined amount of the drug formulation upon each activation. As the formulation is forced from the container through the dose metering valve by the high vapor pressure of the propellant, the propellant rapidly vaporizes, leaving a fast-moving cloud of very fine particles or droplets of the drug formulation. This cloud is then directed into the mouth of the patient. Concurrently with the activation of the aerosol dose metering valve, the patient inhales the drug formulation particles into the lungs. Systems for dispensing drugs in this way are known as metered dose inhalers (MDIs).

For liposomes, the MDI apparatus uses a conventional pressurized propellant spray device for delivering a metered amount of dried liposomes which are suspended in the propellant. Since the system requires long-term suspension of liposomes in a suitable propellant, the liposomes and propellant components of the suspension must be selected for liposome stability on storage. Consistent with this, the lipids chosen must be such that the dried liposomes remain integral in the propellant solvent at the anticipated storage temperature of the pressurized solvent. This condition is usually met by the constraints imposed by the spray drying process.

In one method, the drug is dissolved in a suitable solvent which can be aerosolized to form a small-particle mist. The drug solution may be aerosolized by pneumatic or ultrasonic nebulizer, or more conveniently, by means of a self-contained nebulizer containing a pressurized, fluorocarbon propellant (i.e., liquefied gas). Inhalation of the aerosol mist, i.e., drawing the mist from the mouth or nose into the respiratory tract, acts to deposit the drug-containing aerosol particles on various sites of the respiratory tract, including the upper nasopharyngeal region, the tracheobronchial region, and the pulmonary region. In the latter region, the drug has the opportunity for rapid absorption into the bloodstream for systemic action.

Also well known in the prior art are inhalation systems in which a drug is administered in particulate form, either as a dry powder or as a micronized suspension in a suitable carrier solvent system. Typically the drug is a water-soluble compound which is suspended in micronized form in a fluorocarbon-type propellant solvent. Following aerosolization, most of the propellant solvent is lost through flash evaporation.

EXAMPLES

The invention may be better understood by reference to the following examples, which serve to illustrate but not to limit the present invention.

Example 1

Preparation of Liposomes

Two different types of liposomes were prepared. One type of liposome had, attached to its surface, polyethylene glycol (PEG) as a tether (MW=2000) with a —COOH group (i.e., reactive chemical group), attached to the end of the PEG molecule that was not attached to the liposome. The second type of liposome had, attached it its surface, PEG tethers with an —NH$_2$ reactive chemical group attached to the end of the PEG molecule not attached to the liposome. To make these liposomes, a 10 ml solution containing 20 mM of total lipid was prepared. The breakdown of lipid in the solution was 40% cholesterol (30.9 mg, MW 386.7), 55% dipalmityl phosphatidyl choline (DPPC) (80.7 mg, MW 734) and 5% of either DPPE-PEG—COOH (dipalmityl phosphatidyl ethanolamine)(30.9 mg, MW 2741.46) conjugate or DPPE-PEG-NH$_2$ conjugate (27.1 mg, MW 2713.46). The components were dissolved in 1 ml of ethanol and warmed to 49° C. Nine ml of MES buffer was also warmed to 49° C. The MES buffer was then added to the lipids in the ethanol (i.e., the lipids were hydrated) and the mixture was incubated at 49° for an additional 30 min. The lipid mixture was then extruded through a 0.2 µM Lipex membrane filter 10 times to obtain liposomes of 0.2 microns in size. The extruded liposomes were then dialyzed twice in 1000 ml of 0.45% saline. After dialysis, the molarity of the lipid solution was reduced by adding 2.3 ml of 100 mM MES buffer. The salinity of the final solution was 1.35%.

Figure 5:
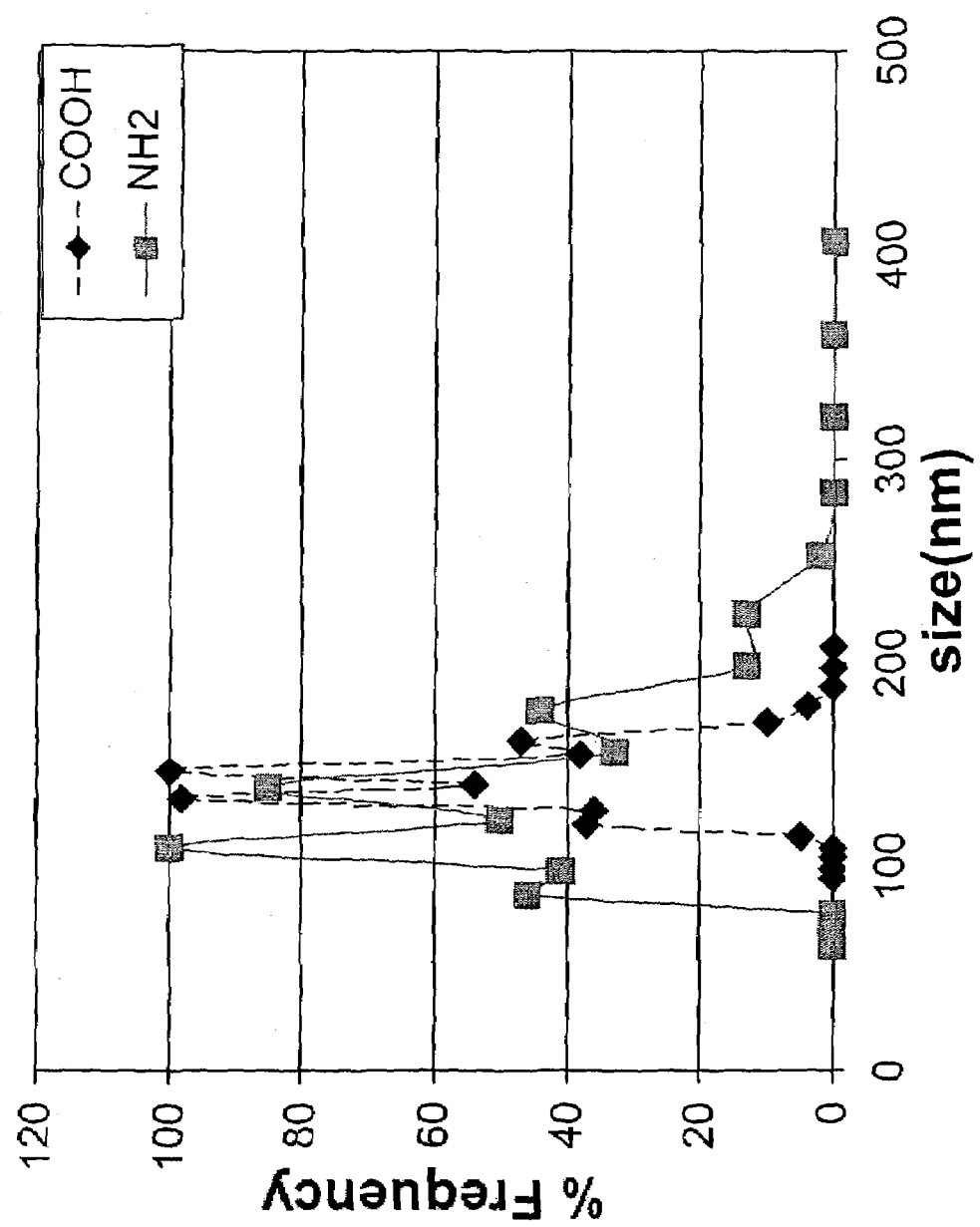

The two sets of liposomes were analyzed by dynamic light scattering (DLS) to determine the size distribution of the liposomes. See FIG. 5. The data show that the mean size of the liposomes is between 100 and 200 nm in diameter.

Example 2

Making Liposome Agglomerates

Figure 6:
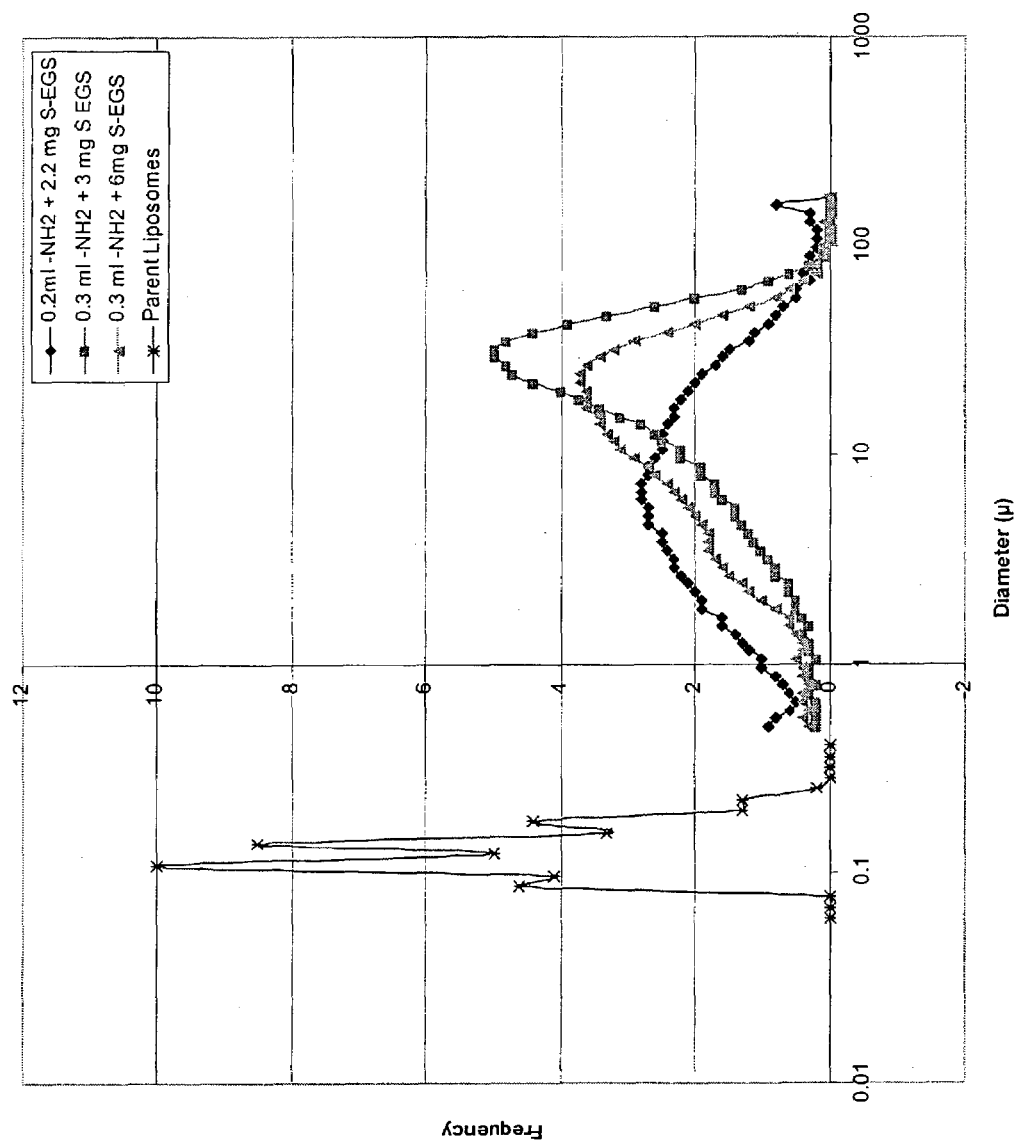

Reactions were performed using the liposomes described in Example 1 above to crosslink the liposomes and form agglomerates. In one reaction, only NH$_2$ liposomes were used. These liposomes were crosslinked to one another using sulfo-[ethylene glycobis(succinimidylsuccinate)], also called S-EGS. In one reaction, 0.2 ml of NH$_2$ liposomes (approximately 6.7×10$^{10}$ liposomes) and 2.2 mg of S-EGS were mixed in a total of 10 ml of phosphate buffer. In a second reaction, 0.3 ml of NH$_2$ liposomes (approximately 1×10$^{11}$ liposomes) and 3 mg of S-EGS were mixed in 10 ml of phosphate buffer. In a third reaction 0.3 ml of NH$_2$ liposomes and 6 mg of S-EGS were mixed in 10 ml of phosphate buffer and reacted overnight at room temperature. For the agglomeration, a 50–150-fold molar excess of sulfo-EGS was used over the NH$_2$ groups. The three sets of agglomerated liposomes were analyzed by Fraunhofer diffraction to determine the size distribution of the agglomerates. See FIG. 6. The data show a mean diameter of the agglomerates of between about 10 and 50 microns. The diameter of liposomes that were not agglomerated was about 0.1 to 0.5 microns.

Figure 11:
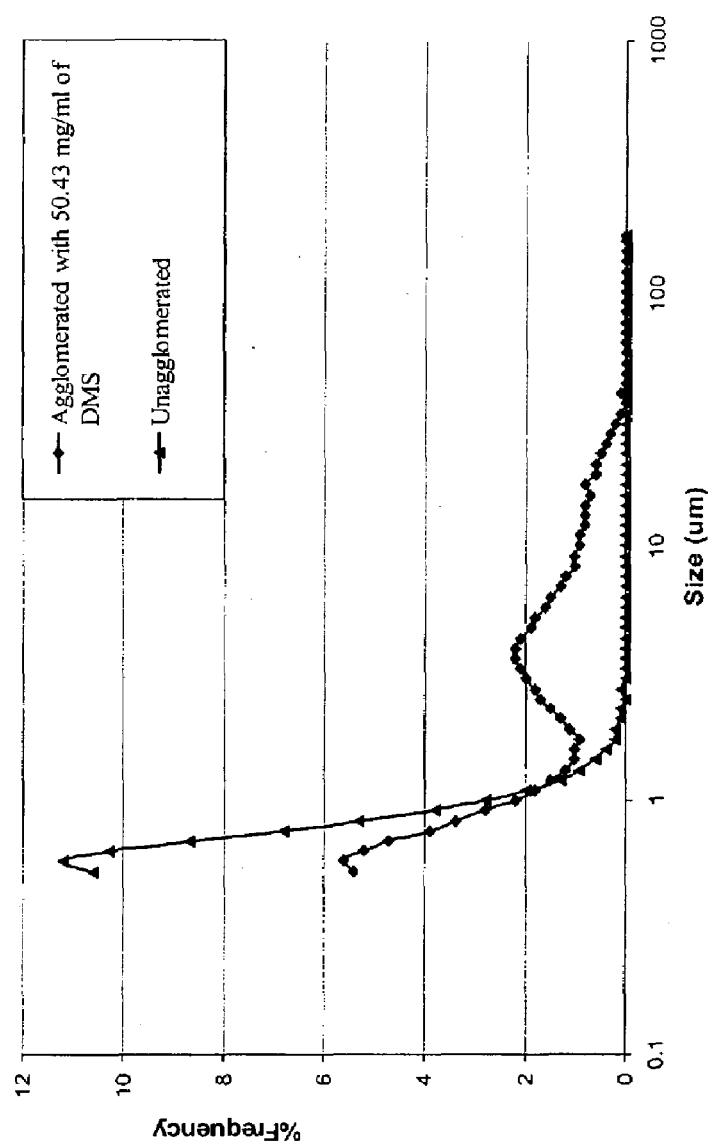

In other studies, NH$_2$ liposomes were agglomerated using DMS (Dimethyl suberimidate•2 HCl). DMS is a homobifunctional imidoester that can react with primary amines and form stable covalent bonds between them. The coupling reaction of the amines with DMS was carried out in the pH range of 7–10 in PBS or citrate-saline buffer. The amount of DMS used was 80–300 fold molar excess of the NH$_2$ groups on the PEG. The DMS was dissolved in buffer immediately before being added to a known volume of liposomal suspension. The reaction mixture was constantly stirred at room temperature. When these agglomerates were analyzed by Fraunhofer diffraction to determine the size distribution of the agglomerates (FIG. 11), it was seen that sizes of the agglomerated particles fell into two areas. One peak included particles of size smaller than 1 µm, representing the remaining parent liposomes or possibly low aggregated agglomerates. The other peak included the agglomerates having sizes between 2–30 µm. This peak shows its maximum at 4 µm.

Figure 12:
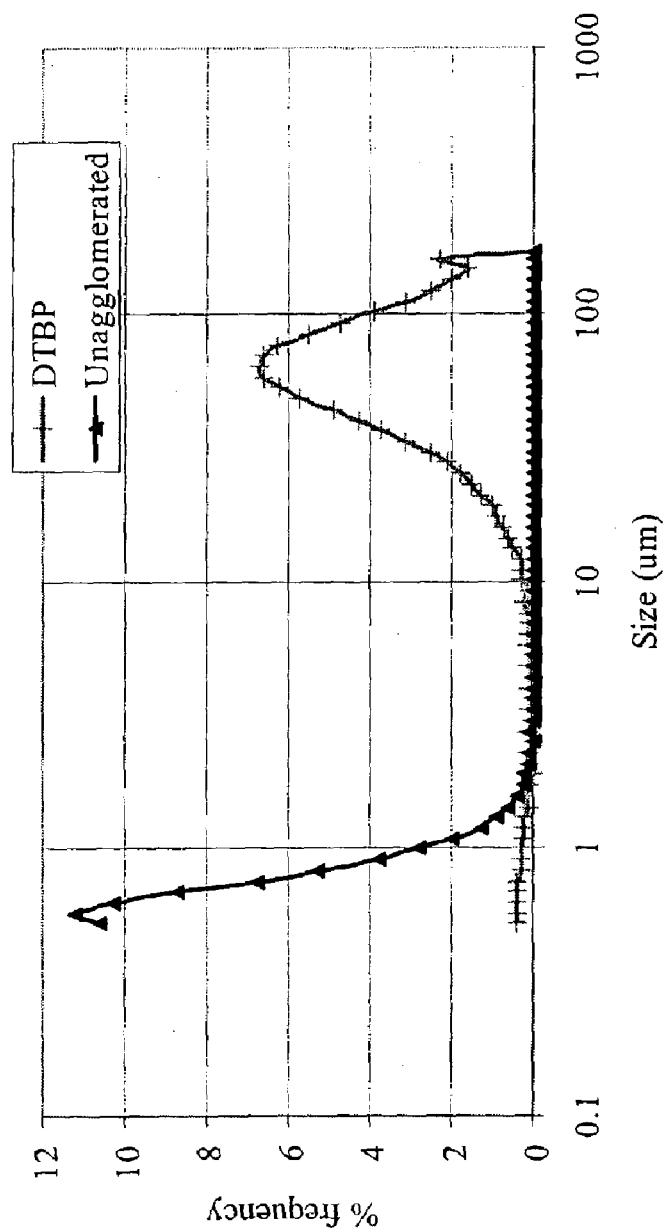

In other studies, $NH_2$ liposomes were agglomerated using DTBP (Dimethyl 3,3'-dithiobispropionimidate•2HCl). DTBP is a homobifunctional imidoester similar to DMS with the only difference being it is thiol-cleavable. For the agglomeration, a 150–440 fold molar excess of DTBP over the $NH_2$ groups on the PEG was used. When these agglomerates were analyzed by Fraunhofer diffraction to determine the size distribution of the agglomerates (FIG. 12), large agglomerates exhibiting sizes between 15–150 µm were seen. This peak has a maximum at 70 µm. In this particular study, a peak for unagglomerated particles does not appear, implying that the majority of the parent liposomes were agglomerated.

Example 3

Encapsulation of Insulin by Liposomes and Formation of Agglomerates

A mixture was made by dissolving 10 mg (of insulin in 9 ml of 0.9% NaCl, pH 2.6. A separate mixture was made by dissolving DPPE-PEG-$NH_2$ conjugate (MW 2713.46) in 1 ml of Ethanol to make a 20 mM solution. The two mixtures were heated separately in a water bath until the lipids were dried. The dried lipids were then hydrated by mixing with the insulin solution. The liposomes that were formed were extruded through a 0.2 micron membrane ten times. After extrusion, the pH was adjusted to 5.1 using HCl or NaOH in order to cause precipitation of both free as well as encapsulated insulin. The precipitated free insulin was separated from the liposomes by passing the suspension through a 0.8 µm filter causing the precipitate to be retained on the filter. Dialysis was then used to remove ethanol and remaining insulin in the external phase [Spectra/Por biotech cellulose ester membranes (100,000 Dalton MWCO) from Fisher Scientific]. The liposomes were then dialyzed against citrate buffer. The size of the liposomes was measured by DLS and shown to be approximately 0.2 microns in diameter.

Figure 10:
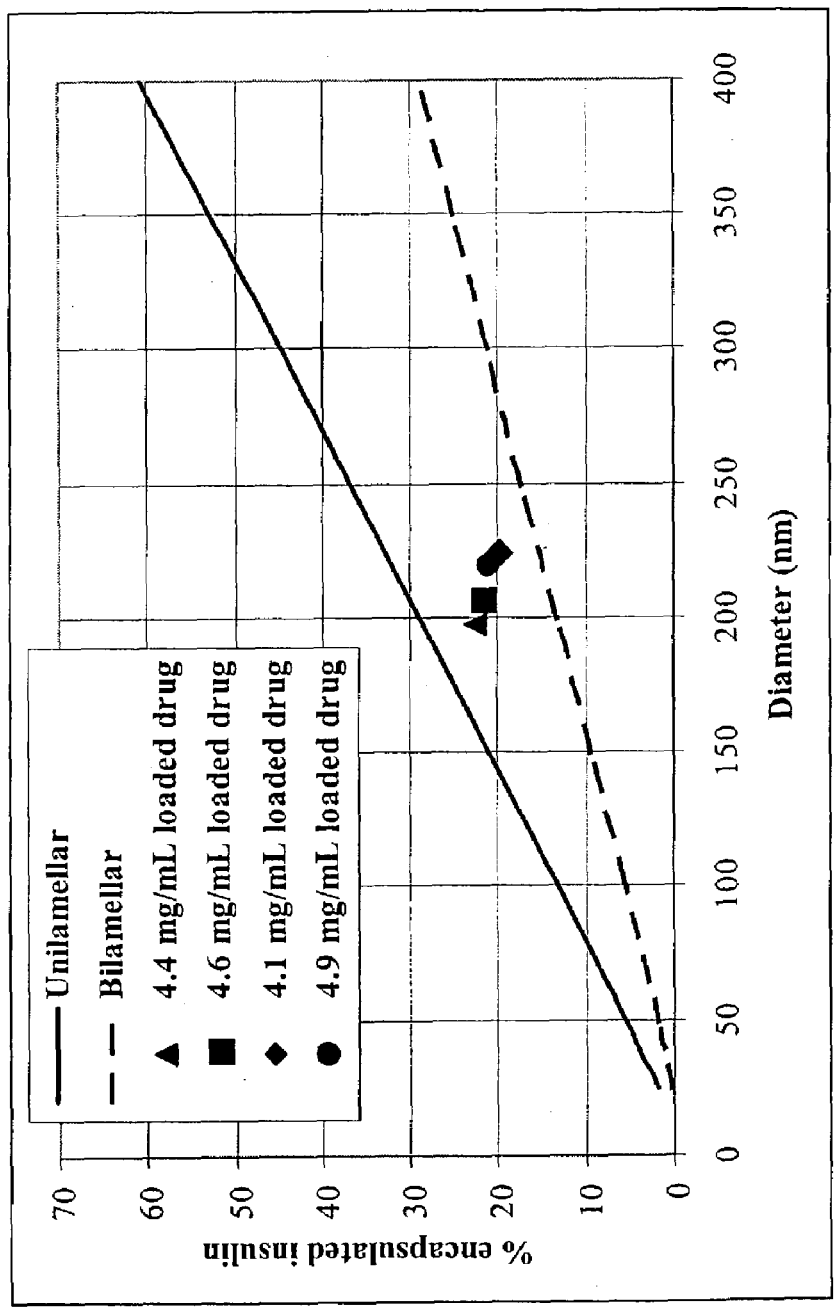

Before the liposomes were agglomerated, the amount of insulin encapsulated into them was measured. Insulin encapsulation was measured by lysing the liposomes with 30% methanol by volume and assaying the total insulin by HPLC. The results were compared against theoretical encapsulation predictions based on the assumption that the bilayer has a thickness of 4 nm, and each molecule has a cross-sectional area in the bilayer of 0.65 $nm^2$. From FIG. 10, it can be seen that the amount of encapsulated drug in the liposomes lies between that for the theoretical values for unilamellar and bilamellar liposomes.

The 10 ml sample of liposomes was then dialyzed against 300 ml of 0.9% NaCl, pH 2.6 and then against 1000 ml of phosphate buffer overnight. 0.3 ml of the liposomes were then agglomerated using S-EGS as described above in Example 2. The size of the agglomerates was measured using Fraunhofer diffraction also as above and shown to be approximately 30 microns in diameter.

Figure 7:
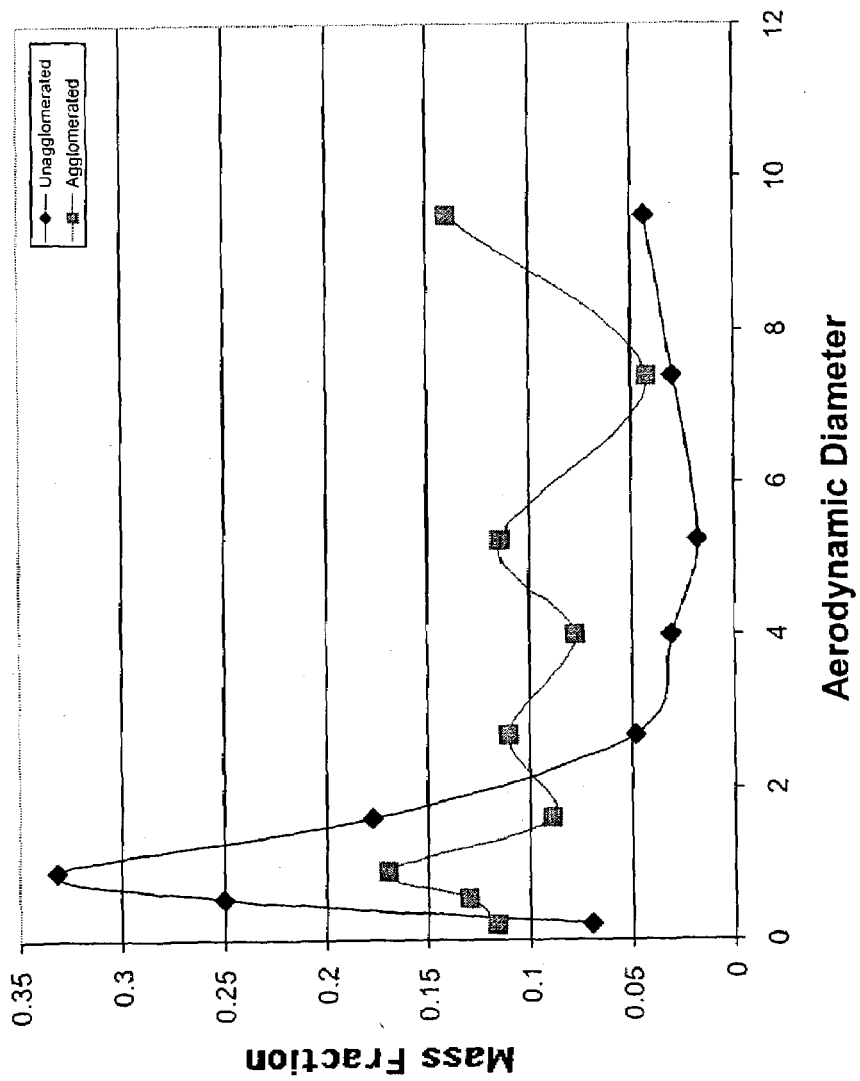

The aerodynamic diameter of the agglomerates was measured. Agglomerates were nebulized, using a nebulizer, into an Andersen cascade impactor instrument. As a control, liposomes that had not been agglomerated were also nebulized into the cascade impactor. Then, for each experiment, the cascade impactor plates were collected, the material collected on the plates was removed by washing the plates with a detergent solution. The insulin content of the samples obtained from the plates was measured using ELISA. The data are shown in FIG. 7 and show that 50% of the agglomerates are in the respirable range (between 1–5 µm).

Figure 13:
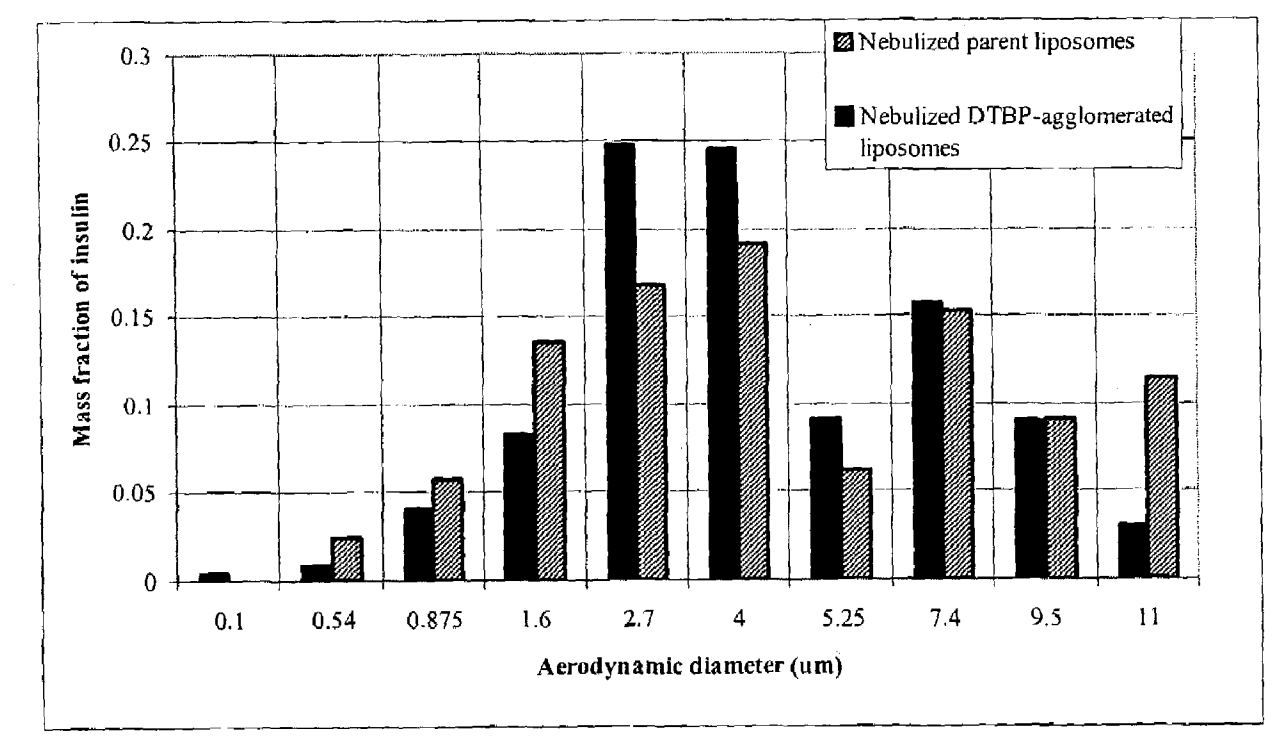

In another study, insulin-containing liposomes were agglomerated using DTBP, as described in Example 2. The size distribution of these agglomerates, measured by Fraunhofer diffraction, was between 10–90 µm. The aerodynamic diameter distribution, as measured by cascade impactor, is shown in FIG. 13. The results show that the aerodynamic diameter of the agglomerates makes them highly respirable. Approximately 70% of the agglomerates had aerodynamic diameters in the respiratory range (between 1–5 µm). These diameters are clearly much lower than the geometrical diameters measured by the Fraunhofer technique.

Example 4

Stability of Insulin-Containing Agglomerates During Nebulization

Figure 14:
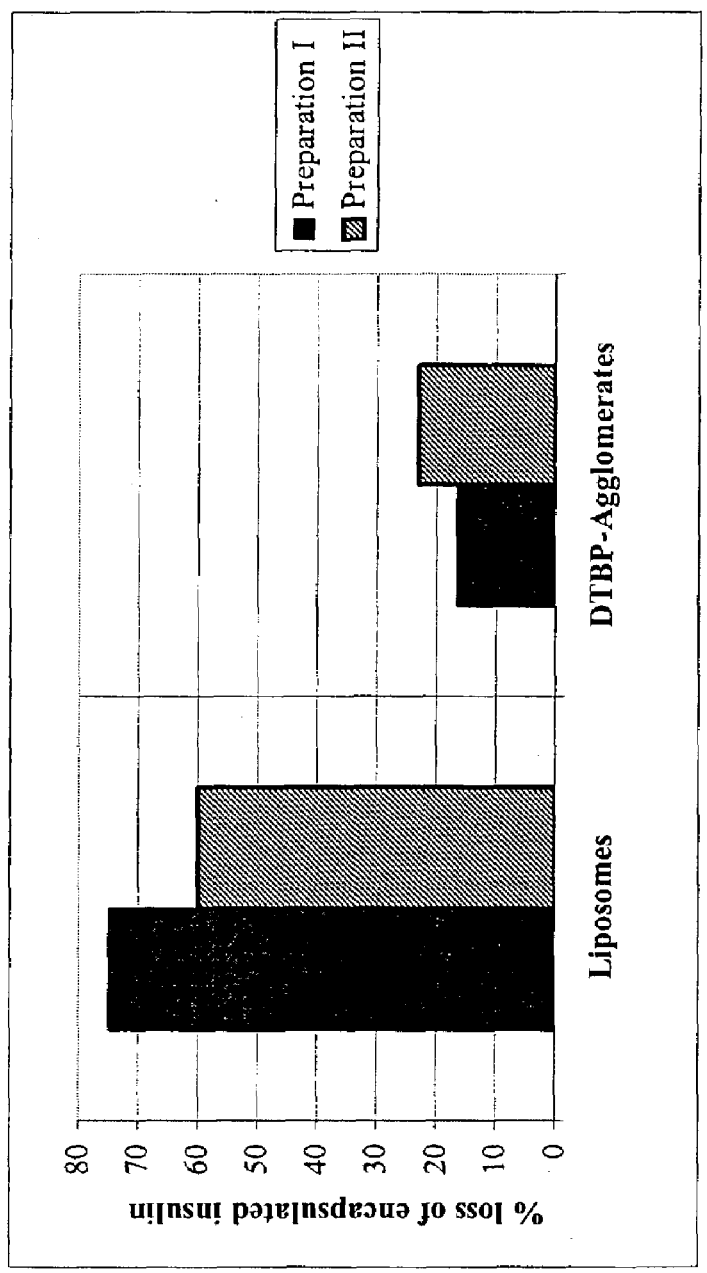

To investigate the stability of agglomerates during nebulization, the fraction of insulin remaining encapsulated after nebulization was measured. A DTBP-agglomerated formulation (and unagglomerated control liposomes) of liposomes containing insulin was nebulized using a Parijet LC nebulizer. The nebulisate was collected in a conical flask which contained citrate buffer. In all the cases, around 20% of the nebulized formulation (both parent liposomes and unagglomerated liposomes) was collected. The loss of encapsulated drug was evaluated by dialysis of the collected nebulisate. The results are shown in FIG. 14 and compare the fraction of the encapsulated insulin for each of the preparations. The results show about 80% loss of encapsulated drug in the case of the liposomes, but the agglomerated formulations show a comparatively lower loss of encapsulated drug. Specifically, only ~20% of the encapsulated insulin leaked out from the DTBP-agglomerates. These data indicate that the agglomerates remain largely intact upon nebulization.

Example 5

Cleavage of Agglomerate Crosslinks

Figure 9:
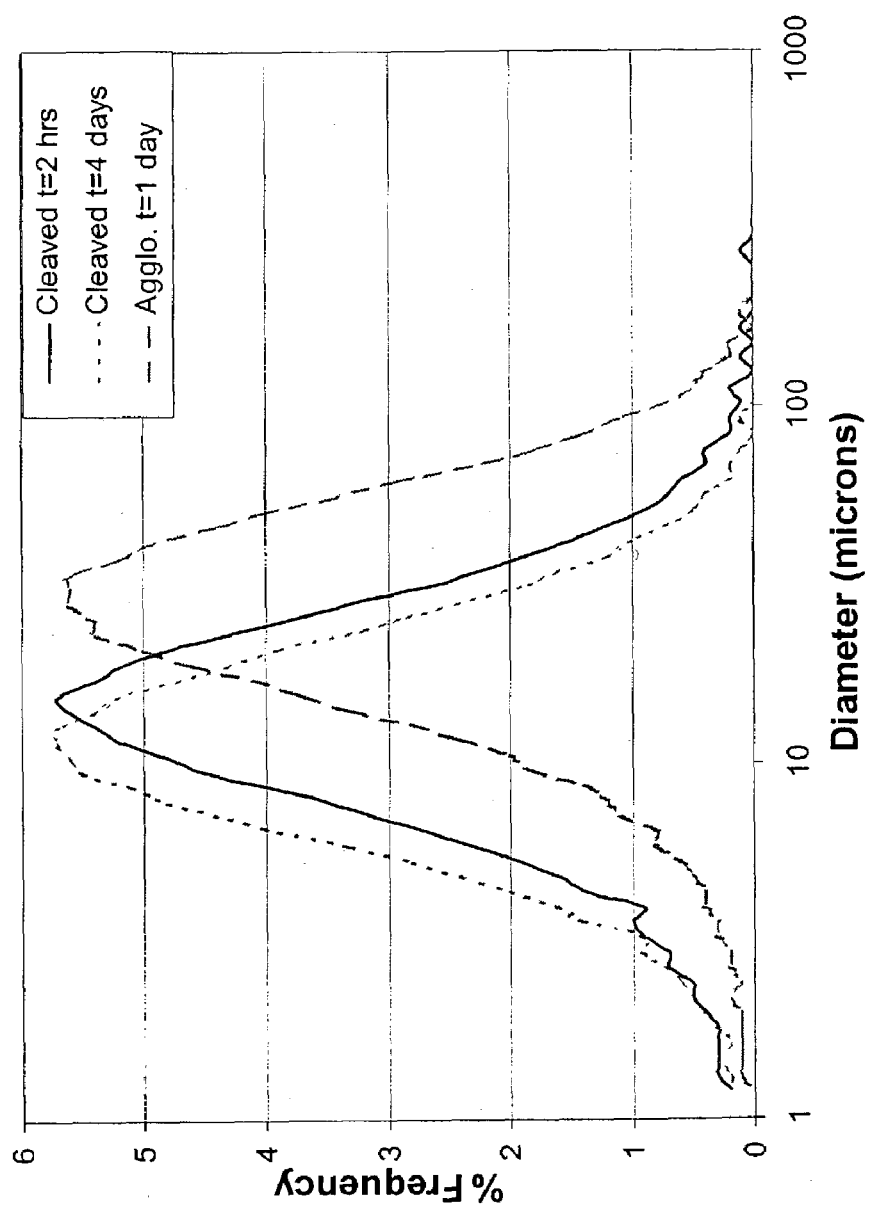

Polystyrene latex particles were agglomerated using a cleavable EGS chemistry as described earlier for the agglomeration of liposomes. The resulting agglomerates (with a Fraunhofer mean diameter around 80 microns) were incubated in a carbonate-bicarbonate buffer at pH 8.4 and treated with 1.2% v/v hydroxylamine. The agglomerates were characterized by Fraunhofer diffraction, and the resulting size distributions are shown in FIG. 9. The data show that the size of the agglomerates dropped continuously with time, as the cleavage of the crosslinks occurred. Such cleavage of the crosslinks of agglomerates increases the rate at which drug is released from the particles since an enhanced surface area is exposed to the release medium.

Figure 15:
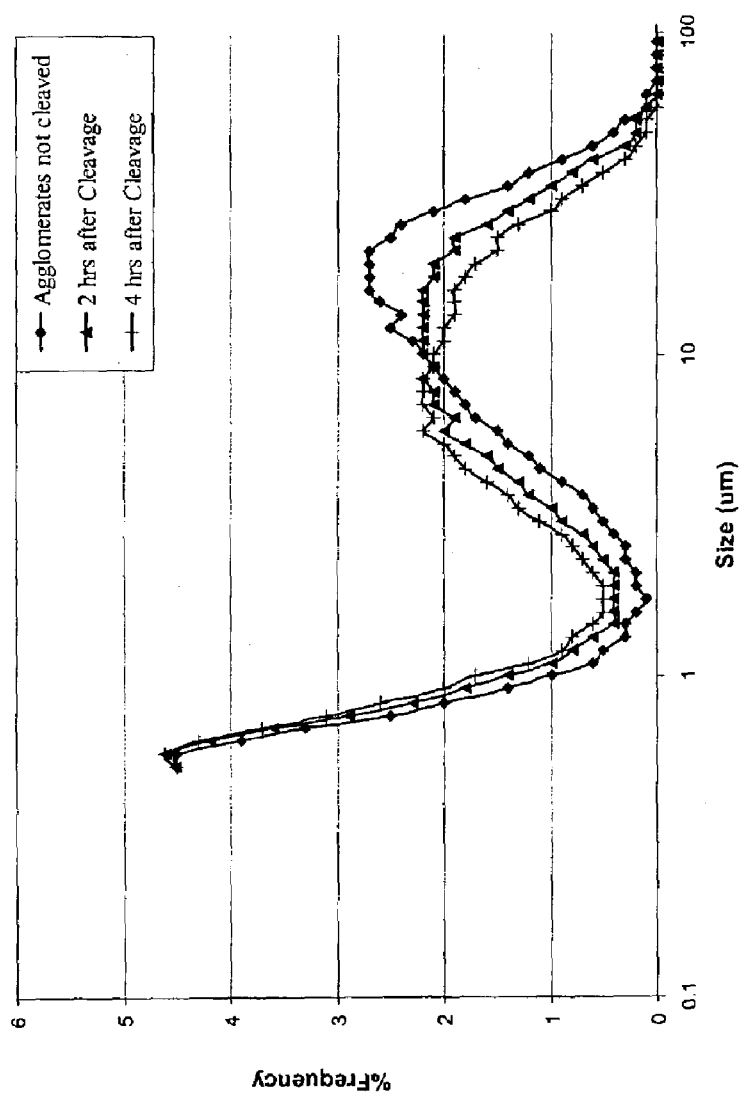

In another study, the cleavage of DTBP agglomerated liposomes was examined. Cleavage of the DTBP agglomerates was accomplished with Dithiothreitol (DTT) at 37° C. The data (FIG. 15) show a reduction in agglomerate size with time of cleavage.

Example 6

Rate of Release of Insulin from Liposome Agglomerates

Figure 8:
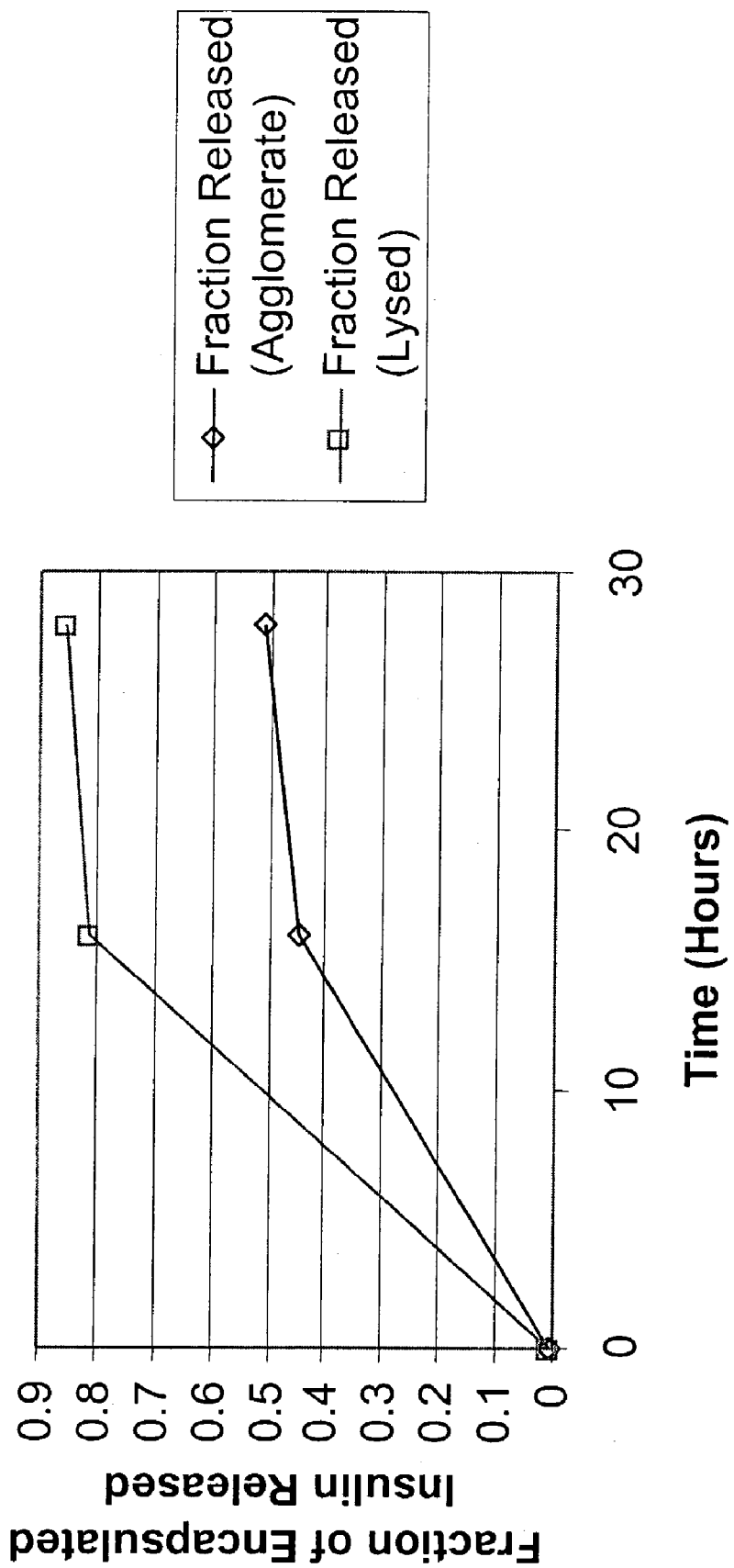

The agglomerates of insulin-containing liposomes agglomerated with S-EGS as described in Examples 2 and 3 were incubated in a phosphate-buffered saline solution at pH 7.2. The external phase was separated from the liposomes by dialysis through a 100,000 molecular weight cutoff membrane at specific time intervals and analyzed by UV absorption. The amount of insulin that passed through the dialysis membrane was equal to that released from the agglomerates, since the agglomerates themselves were too large to pass through the membrane. An identical experiment was also performed where the liposomes were lysed with a 10% V/V solution of Tween-20 (a commercial surfactant) to simulate rapid reassembly of the liposomes after pulmonary administration. The data are shown in FIG. 8 and show a slower release of insulin from agglomerates as compared to reassembled liposomes.

In a series of experiments described below, the in vitro release of insulin from different formulations was also evaluated. In these studies, the commercial pulmonary surfactant replacement Survanta® (Abbott Laboratories) was used to simulate the lung environment. Drug preparation and Survanta® (3:1 volumetric ratio respectively) were incubated at 37° C. in a dialysis bag (300,000 MWCO) immersed in citrate buffer at a pH of 7.4. Samples from the external phase were taken and were assayed for insulin in the HPLC.

Figure 16:
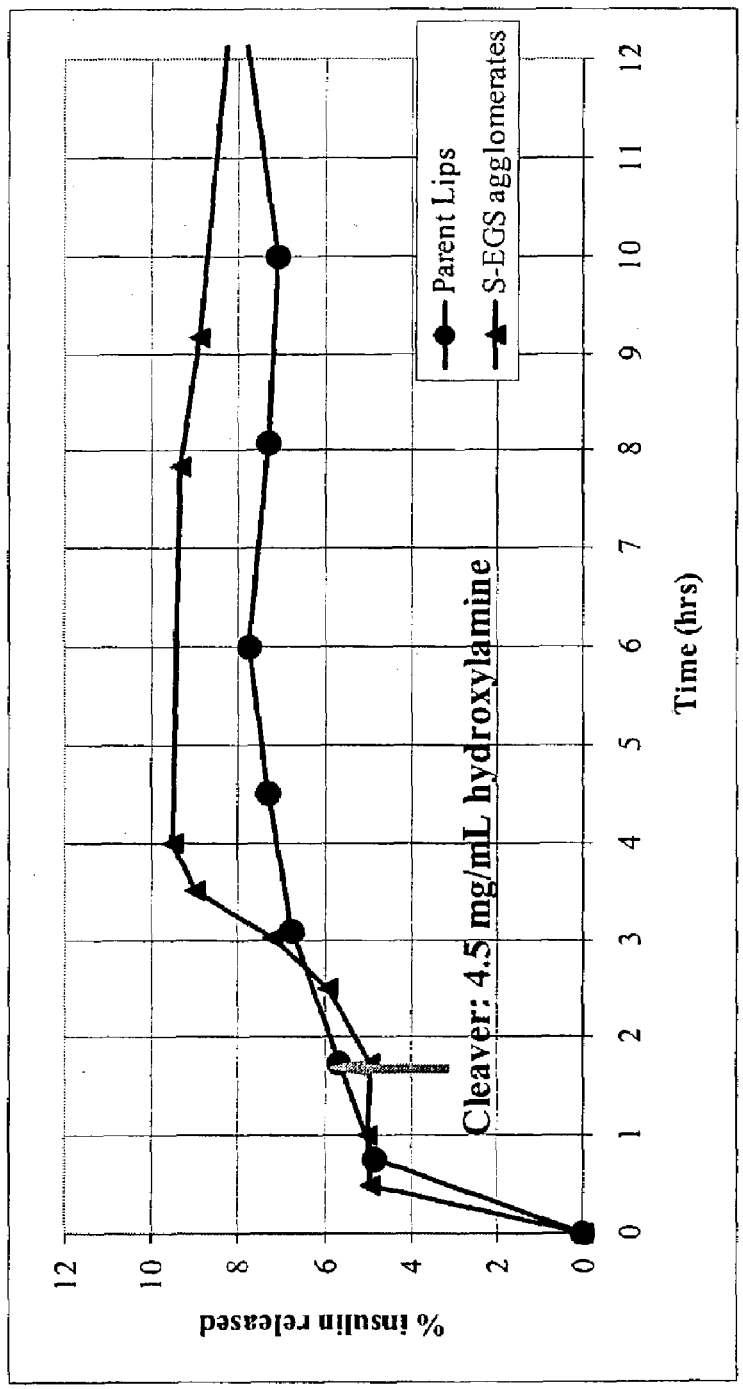

FIG. 16 shows a comparison between the release of insulin from parent liposomes and sulfo-EGS-agglomerates. The release of insulin from the core liposomes showed a starting burst during the first half hour and then gradually leveled off. The sulfo-EGS-agglomerates exhibited a similar initial burst. When the release reached a plateau, the agglomerates were cleaved by incubating with 4.5 mg/mL of hydroxylamine. The introduction of the cleaver clearly caused an acceleration of the insulin release. Two hours after the introduction of hydroxylamine, the release was almost doubled. Then the release reached a plateau, which was followed by a gradual decrease due to degradation.

Figure 17:
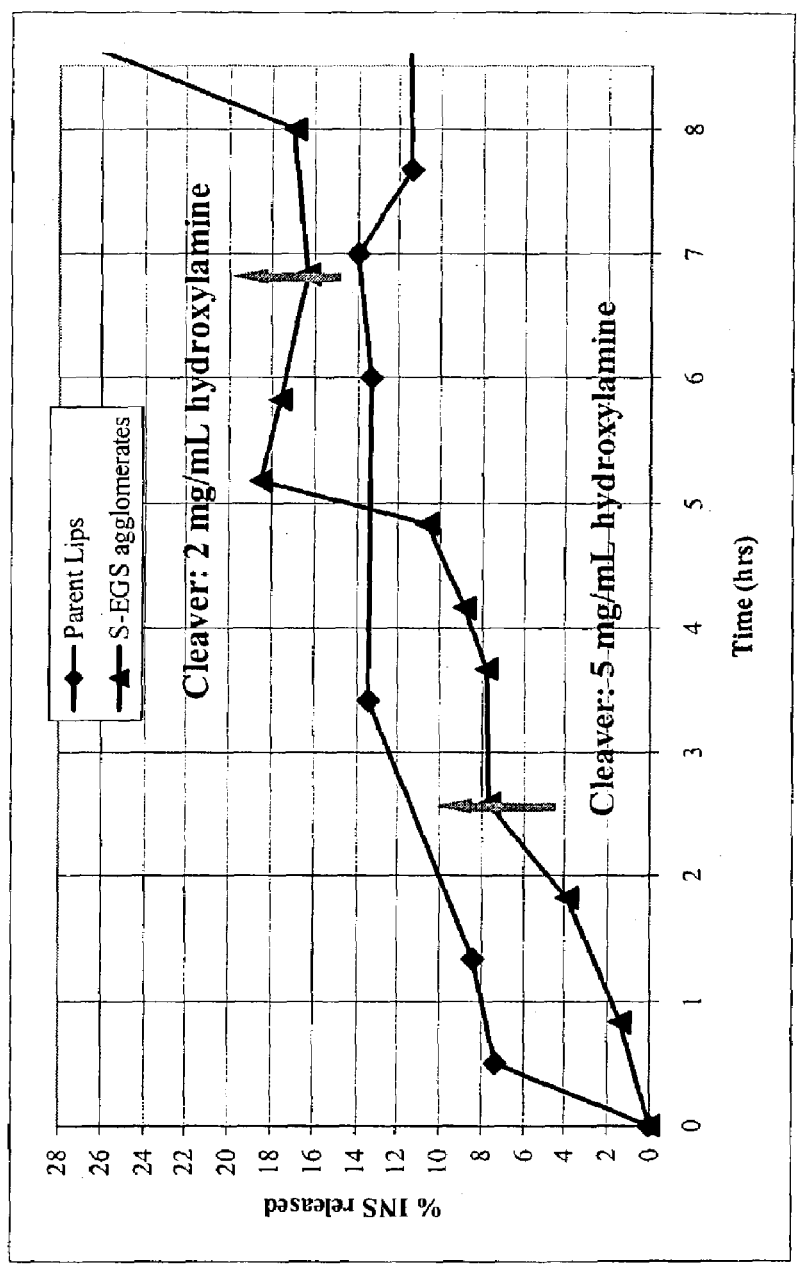

A release profile of insulin caused by multiple applications of the cleaving agent is shown in FIG. 17. The release from the parent liposomes showed an initial burst and gradually reached a plateau after 4 hours. In the case of sulfo-EGS-agglomerates, release was accelerated after hydroxylamine was added. One and a half hours after the addition of the cleaver, the release was more than doubled. After the release reached a plateau, further cleavage occurred by adding more cleaver. The release was again clearly accelerated The studies shown in FIGS. 16 and 17 were performed at 37° C. over an extended period of hours. Under these conditions, degradation of insulin was expected due to the presence of proteolytic enzymes in the surfactant. Therefore, the insulin monitored in the external phase of the dialysis membrane was less than the actual release. This was verified at the end of each study when the formulation was collected from the dialysis bag and the remaining insulin was measured. In all the cases the actual insulin missing from the liposomes was 2–3 times more than the insulin measured as released. This indicates that insulin release, as shown in FIGS. 16 and 17, was actually greater than shown.

Figure 18:
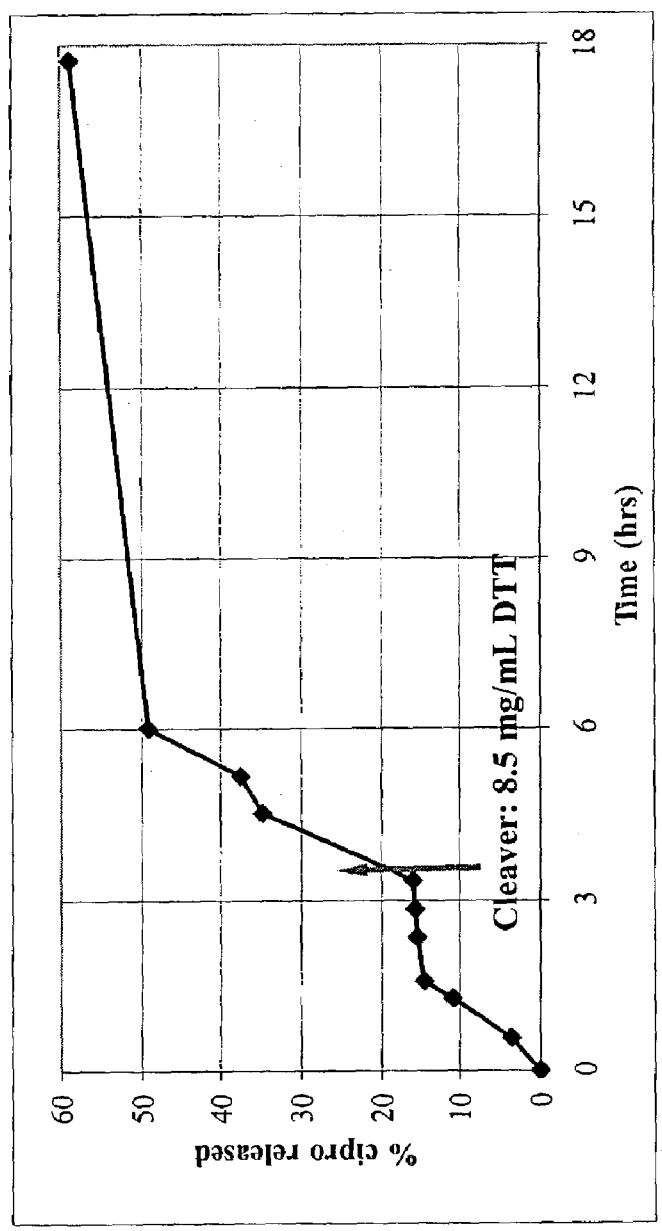

FIG. 18 shows the release of ciprofloxacin from DTBP-agglomerates. Ciprofloxacin was remotely loaded into liposomes of 50 mM lipid content. Blank liposomes were prepared in a 400 mM ammonium sulfate unbuffered solution. The liposomes were dialyzed (using 10,000 MWCO dialysis tubing) for 2 hours against 250 mL of deionized water in order to remove ethanol and ammonium sulfate from the external phase of the liposomes. Ciprofloxacin was dissolved in deionized water at pH 5.5 and 50° C. The solution of ciprofloxacin was added into the liposomal suspension and the temperature was maintained at 52° C. The remote loading procedure was terminated after 1 hour by rapidly dropping the temperature using an ice bath. Then, the suspension was separated from untrapped ciprofloxacin by dialyzing the liposomal suspension for 4 hours against 300 mL of deionized water at pH 5.5. The liposomes were agglomerated using the DTBP chemistry, described in Example 2.

FIG. 18 shows that the monitored release in this case was much higher than in the case of insulin, since ciprofloxacin does not degrade in lung surfactant to the same extent as insulin. Therefore, the monitored release is considered to be closer to the actual release. After the initial burst, the release of the drug from the agglomerates reached a plateau. The addition of DTT caused cleavage, which was assumed complete, since a 20-fold molar excess of cleaver was used. Cleavage resulted in a release of 35% of the encapsulated drug in less than three hours after the addition of the cleaver.

In all of the studies described above, it was observed that the agglomerates after cleavage released more drug than the parent liposomes.

It should be understood that the preceding is merely a detailed description of preferred embodiments. It therefore should be apparent to those of ordinary skill in the art that various modifications and equivalents can be made without departing from the spirit and scope of the invention. All references, patents and patent publications that are identified in this application are incorporated in their entirety herein by, reference. The specific examples presented above are illustrative only and are not intended to limit the scope of the invention described herein.

We claim:

1. A drug delivery vehicle exhibiting controlled release of drugs when incubated in a physiological environment, the drug delivery vehicle comprising:
   an agglomerate of at least two biocompatible particles loaded with one or more drugs;
   wherein the biocompatible particles are liposomes that have a plurality of reactive groups associated with the surfaces thereof and are chemically cross-linked by a covalent bond or spacer to one another to form the agglomerate of two or more particles; and
   wherein the agglomerate is of a size capable of being inhaled by a mammalian subject.

2. The drug delivery vehicle of claim 1 wherein the biocompatible particles are formed from a material that is bioresorbable or biodegradable.

3. The drug delivery vehicle of claim 1 wherein the agglomerates have an aerodynamic diameter of between 1 and 10 microns.

4. The drug delivery vehicle of claim 1 wherein one or more of the reactive chemical groups are directly attached to the surface of a particle.

5. The drug delivery vehicle of claim 1 wherein one or more of the reactive chemical groups are attached to the particle through a tether molecule.

6. The drug delivery vehicle of claim 1 wherein two or more of the biocompatible particles that form the agglomerate are chemically cross-linked via a spacer.

7. The drug delivery vehicle of claim 1 wherein two or more of the biocompatibic particles that form the agglomerate are cross-linked by a cleavable covalent bond or spacer.

8. The drug delivery vehicle of claim 1 wherein two or more of the particles that form the agglomerate are cross-linked by a non-cleavable covalent bond or spacer.

9. A pharmaceutical composition comprising one or more drug delivery vehicles of claim 1, wherein the pharmaceutical composition is in a form that is capable of being inhaled by a mammalian subject.

10. The pharmaceutical composition of claim 9 wherein the pharmaceutical composition is in the form of an oral aerosol.

11. The pharmaceutical composition of claim 9 additionally comprising one or more substances that is capable of cleaving one or more covalent bonds or spacers that cross-link two or more particles in the agglomerate.

12. The pharmaceutical composition of claim 9, wherein the pharmaceutical composition comprises one or more ingredients selected from the group consisting of a solvent, a propellant, a sugar, a salt a buffering agent, a preservative, a pharmaceutically-acceptable carrier, an excipient, and a therapeutic agent.

* * * * *